US011651857B2

(12) United States Patent
Nye et al.

(10) Patent No.: US 11,651,857 B2
(45) Date of Patent: *May 16, 2023

(54) METHODS AND APPARATUS TO CAPTURE PATIENT VITALS IN REAL TIME DURING AN IMAGING PROCEDURE

(71) Applicant: General Electric Company, Schenectady, NY (US)

(72) Inventors: Katelyn Rose Nye, Waukesha, WI (US); Gireesha Rao, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/921,919

(22) Filed: Jul. 6, 2020

(65) Prior Publication Data
US 2020/0335205 A1 Oct. 22, 2020

Related U.S. Application Data

(63) Continuation-in-part of application No. 16/197,795, filed on Nov. 21, 2018, now Pat. No. 10,706,602.

(51) Int. Cl.
*G16H 30/40* (2018.01)
*G06T 7/00* (2017.01)
(Continued)

(52) U.S. Cl.
CPC ........... *G16H 30/40* (2018.01); *G06T 7/0012* (2013.01); *G16H 40/60* (2018.01); *G16H 50/20* (2018.01);
(Continued)

(58) Field of Classification Search
None
See application file for complete search history.

(56) References Cited

U.S. PATENT DOCUMENTS 5,441,047 A * 8/1995 David ................. A61B 5/6887
348/93
6,151,521 A * 11/2000 Guo ..................... A61B 5/7425
600/407

(Continued)

FOREIGN PATENT DOCUMENTS

WO WO-2010106449 A2 * 9/2010 ............. A61B 5/743

OTHER PUBLICATIONS

United States Patent and Trademark Office, "Notice of Allowance," issued in connection with U.S. Appl. No. 16/197,795, dated Mar. 11, 2020, 19 pages.

(Continued)

*Primary Examiner* — Reza Aghevli
(74) *Attorney, Agent, or Firm* — Hanley, Flight and Zimmerman, LLC

(57) ABSTRACT

Apparatus, systems, and methods to capture and combine patient vitals and image data are disclosed. An example apparatus includes an imaging device to capture imaging data of a patient; a patient monitor to capture non-imaging data of the patient; and a communication interface between the imaging device and the patient monitor to route the non-imaging data to the imaging device. The example imaging device is to combine the non-imaging data with the imaging data to form a combined data set to be processed to determine a clinical outcome.

20 Claims, 14 Drawing Sheets

(51) Int. Cl.
 *G16H 50/20* (2018.01)
 *G16H 40/60* (2018.01)
(52) U.S. Cl.
 CPC ............... *G06T 2207/10116* (2013.01); *G06T 2207/20212* (2013.01)

(56) References Cited

U.S. PATENT DOCUMENTS

| | | | | |
|---|---|---|---|---|
| 9,900,517 | B2* | 2/2018 | Hansen | H04N 5/22525 |
| 10,706,602 | B2* | 7/2020 | Nye | G16H 40/63 |
| 2004/0109059 | A1* | 6/2004 | Kawakita | H04N 7/18 |
| | | | | 348/143 |
| 2006/0022834 | A1* | 2/2006 | Rosenfeld | A61B 5/4094 |
| | | | | 600/300 |
| 2006/0155549 | A1* | 7/2006 | Miyazaki | G10L 15/26 |
| | | | | 704/E15.045 |
| 2007/0118389 | A1* | 5/2007 | Shipon | G16H 10/60 |
| | | | | 705/2 |
| 2007/0221849 | A1* | 9/2007 | Tabirian | G01S 17/89 |
| | | | | 250/341.1 |
| 2009/0006132 | A1 | 1/2009 | Avinash | |
| 2009/0124863 | A1* | 5/2009 | Liu | A61B 5/1114 |
| | | | | 600/300 |
| 2010/0234695 | A1 | 9/2010 | Morris | |
| 2011/0299747 | A1* | 12/2011 | Solf | G16H 30/20 |
| | | | | 382/128 |
| 2012/0098971 | A1* | 4/2012 | Hansen | H04N 5/2252 |
| | | | | 348/E5.09 |
| 2012/0098972 | A1* | 4/2012 | Hansen | G06T 11/60 |
| | | | | 348/E5.09 |
| 2012/0158432 | A1 | 6/2012 | Jain et al. | |
| 2012/0290324 | A1 | 11/2012 | Ribbing | |
| 2014/0081659 | A1 | 3/2014 | Nawana et al. | |
| 2014/0112537 | A1* | 4/2014 | Frank | G01N 21/17 |
| | | | | 315/149 |
| 2014/0218520 | A1* | 8/2014 | Teich | H04N 5/332 |
| | | | | 348/165 |
| 2014/0365242 | A1* | 12/2014 | Neff | G16H 10/60 |
| | | | | 707/756 |
| 2014/0366878 | A1* | 12/2014 | Baron | G16H 40/60 |
| | | | | 128/204.23 |
| 2015/0213217 | A1 | 7/2015 | Amaransingham et al. | |
| 2015/0305662 | A1* | 10/2015 | Kilmer | A61B 5/164 |
| | | | | 600/476 |
| 2015/0356144 | A1 | 12/2015 | Chawla et al. | |
| 2015/0356404 | A1 | 12/2015 | Sanchez et al. | |
| 2015/0356427 | A1 | 12/2015 | Sanchez et al. | |
| 2015/0356428 | A1 | 12/2015 | Sanchez et al. | |
| 2016/0037077 | A1* | 2/2016 | Hansen | H04N 5/23296 |
| | | | | 348/164 |
| 2016/0048762 | A1 | 2/2016 | Sanchez et al. | |
| 2017/0011200 | A1 | 1/2017 | Arshad et al. | |
| 2017/0091661 | A1 | 3/2017 | Sanchez et al. | |
| 2017/0231508 | A1* | 8/2017 | Edwards | G16H 40/40 |
| | | | | 600/301 |
| 2017/0374261 | A1* | 12/2017 | Teich | H04N 17/002 |
| 2018/0032692 | A1* | 2/2018 | Hickle | A61B 5/747 |
| 2018/0040123 | A1* | 2/2018 | Neff | G06T 7/0012 |
| 2018/0052968 | A1* | 2/2018 | Hickle | G16H 50/20 |
| 2018/0165416 | A1 | 6/2018 | Saxena et al. | |
| 2018/0165588 | A1 | 6/2018 | Saxena et al. | |
| 2018/0165611 | A1 | 6/2018 | Saxena et al. | |
| 2018/0165758 | A1 | 6/2018 | Saxena et al. | |
| 2018/0247714 | A1* | 8/2018 | Lee | A61B 5/7264 |
| 2018/0272147 | A1* | 9/2018 | Freeman | G16H 50/30 |
| 2019/0006047 | A1 | 1/2019 | Gorek et al. | |
| 2019/0026608 | A1 | 1/2019 | Hsieh | |
| 2019/0206564 | A1* | 7/2019 | Shelton, IV | G06K 7/10316 |
| 2019/0320974 | A1* | 10/2019 | Alzamzmi | G16H 50/20 |
| 2020/0121199 | A1* | 4/2020 | Freeman | G06F 3/14 |
| 2020/0016057 | A1 | 5/2020 | Nye et al. | |
| 2020/0225308 | A1* | 7/2020 | Dosenbach | G16H 30/40 |
| 2020/0335205 | A1* | 10/2020 | Nye | G16H 30/40 |
| 2021/0110901 | A1* | 4/2021 | Cronin | G01R 33/5608 |

OTHER PUBLICATIONS

United States Patent and Trademark Office, "Non-Final Office action," issued in connection with U.S. Appl. No. 16/197,795, dated Oct. 29, 2019, 28 pages.
United States Patent and Trademark Office, "Corrected Notice of Allowability," issued in connection with U.S. Appl. No. 16/197,795, dated May 1, 2020, 11 pages.
European Patent Office, "Search Report," issued in connection with No. 19210474.2, dated Feb. 25, 2020, 13 pages.
EP application 21181597.2 filed Jun. 24, 2021—Extended Search Report dated Dec. 3, 2021; 9 pages.

* cited by examiner

METHODS AND APPARATUS TO CAPTURE PATIENT VITALS IN REAL TIME DURING AN IMAGING PROCEDURE

CROSS-REFERENCE TO RELATED APPLICATIONS

This patent arises from a continuation-in-part of U.S. patent application Ser. No. 16/197,795, (Now U.S. Pat. No. 10,706,602) which was filed on Nov. 21, 2018. U.S. patent application Ser. No. 16/197,795 is hereby incorporated herein by reference in its entirety. Priority to U.S. patent application Ser. No. 16/197,795 is hereby claimed.

FIELD OF THE DISCLOSURE

This disclosure relates generally to image processing, and, more particularly, to capturing and combining patient vitals and image data.

BACKGROUND

In recent years, medical imaging has led to improvements in the diagnosis and treatment of numerous medical conditions of patients. Some types of medical imaging are computed tomography, fluoroscopy, and radiography. These examples work on the same basic principle technique, where a patients is positioned between an X-ray source and an X-ray detector. When the X-ray source is turned on an X-ray beam is passed through the body and a portion of the X-rays are either absorbed or scattered by the internal structures, and the remaining X-ray pattern is transmitted to a detector for recording or further processing by a computer. In radiography, a single image is recorded for later evaluation by a health care provider.

BRIEF SUMMARY

Certain examples provide apparatus, systems, and methods to improve capturing and combining patient vitals and image data.

Certain examples provide an apparatus including an imaging device to capture imaging data of a patient; a patient monitor to capture non-imaging data of the patient; and a communication interface between the imaging device and the patient monitor to route the non-imaging data to the imaging device. The example imaging device is to combine the non-imaging data with the imaging data to form a combined data set to be processed to determine a clinical outcome.

Certain examples provide a tangible computer readable storage medium comprising instructions that, when executed, cause at least one processor to at least: capture imaging data of a patient; capture non-imaging data of the patient via a communication interface between the at least one processor and a patient monitor; combine the non-imaging data with the imaging data to form a combined data set; and facilitate processing of the combined data set to determine a clinical outcome.

Certain examples provide a method including: capturing, using an imaging device, imaging data of a patient; capturing, using the imaging device, non-imaging data of the patient via a communication interface between the imaging device and a patient monitor; combining, using the imaging device, the non-imaging data with the imaging data to form a combined data set; and facilitating processing of the combined data set to determine a clinical outcome.

DETAILED DESCRIPTION

Figure 1:
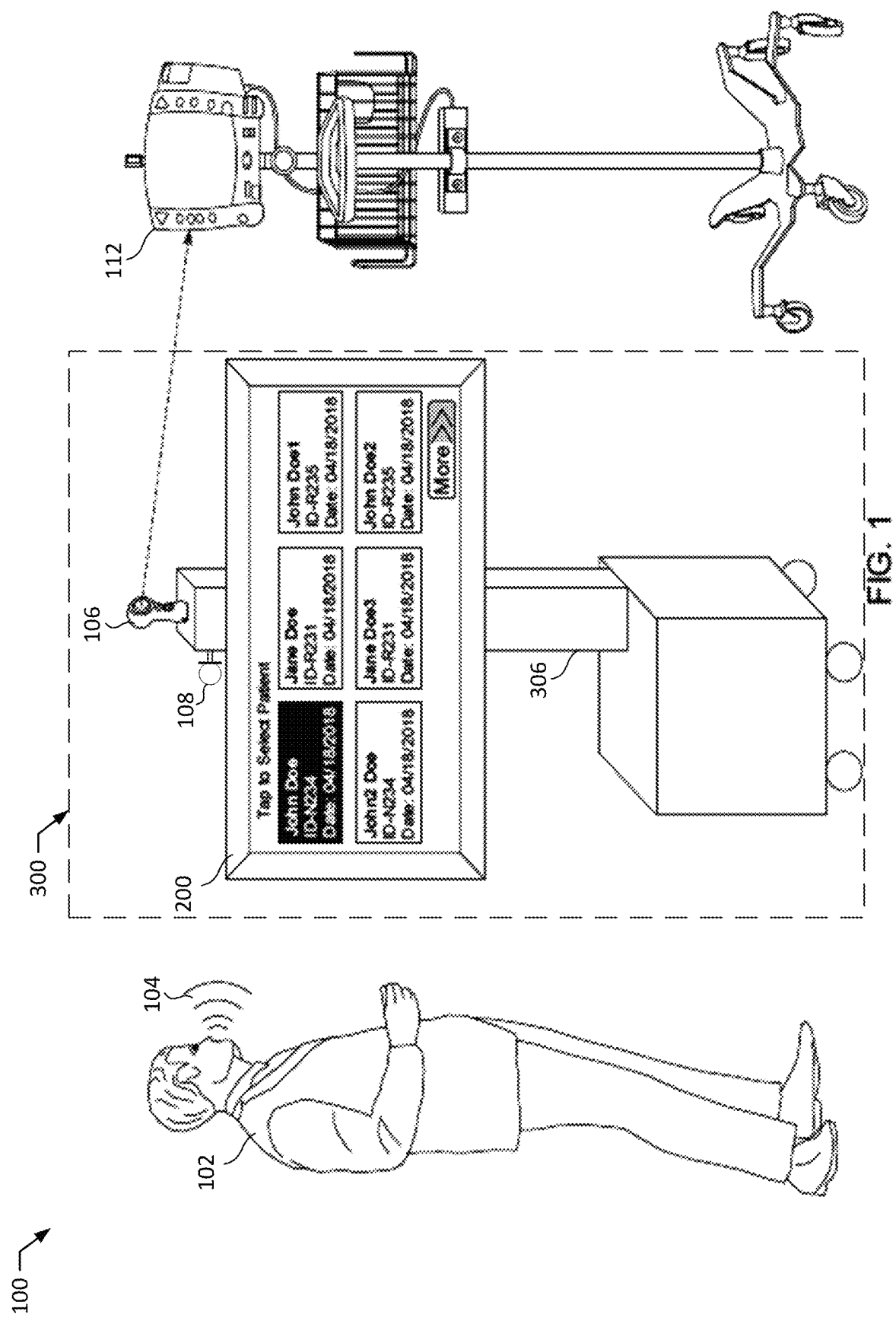
FIG. 1 is an example environment representative of a health care provider room wherein the vitals capturing device and x-ray device are in use.

In hospitals, dental offices, clinics, or other health care providers that specialize in diagnostic procedures, imaging devices, such as X-ray imaging devices, ultrasound imaging devices, magnetic resonance imaging devices, etc., are utilized to examine a patient. X-ray imaging devices are used herein for purposes of example illustration only. Typically, X-rays are taken in a specific environment such as a dark, large, or quiet room. In some examples, when a patient is in critical condition, they are located in an intensive care unit (ICU), emergency room (ER), or operating room (OR), which are located in special department of a health care facility. In each of these locations, a health care provider may want to take an X-ray image of the patient without having to reposition or relocate the patient, in case of worsening the medical condition. The patient in critical condition might be connected to a multitude of machines that determine their vitals (e.g., heart rate, blood pressure, respiratory rate, oxygen saturation, body temperature, etc.), in which all of the measurements are displayed on one vital monitor. This information provided by the vital monitor, along with the results of an x-ray image, are very important for the diagnosis of a patient.

The process of taking an X-ray of a patient to diagnosing the patient begins when the health care provider positions the X-ray device around the patient. The image is captured and sent via some type of imaging technique in which specifies a data interchange protocol, digital file format, and file structure for medical images, such as digital imaging and communications in medicine (DICOM). The image may be produced at a location different from where it was taken. A health care provider who specializes in reading an X-ray image retrieves the image, analyzes it, diagnosis the patient, and proceeds to treat the patient.

For accurate diagnosis of x-ray images, it is desirable for health care specialists to know the patient vitals, especially for diagnosing the patients in critical condition. For example, a small lung collapse in a chest x-ray image, paired with a drop in oxygen means treatment is needed, whereas a large lung collapse that has not affected the oxygen level may require a different treatment. Since the x-ray images are read several hours after the x-ray image was taken, the pertinent vital information is often not available and therefore results in a mis diagnosis or a lot of time spent communicating with other health care specialists to recall patient vital information. In some examples, artificial intelligence algorithms can learn to make similar decisions to diagnose a patient based on a patient's vitals paired with an x-ray image.

Much data can be made available at a point of care, but systems are focused on a particular type of data, unable to capture other information also available at the point of care. For example, an x-ray system captures x-ray exposure and/or other light intensity data received at its detector but captures no other information related to the patient or the patient's environment. Certain examples enable the x-ray system to capture a plurality of types of data. Certain examples enable the x-ray system to capture information in addition to x-ray exposure data during and around an imaging procedure at a point of care. Certain examples provide an x-ray radiology device that serves as an interception point to gather patient monitor information audibly, visually, and/or electronically available within range of the x-ray device.

In certain examples, a communication interface (e.g., Wi-Fi, Bluetooth™, Near Field Communication (NFC), universal serial bus (USB), ethernet, open natural interaction (OpenNI), natural user interface (NUI), etc.) is included in or with the x-ray machine to capture vitals data, environmental data, other patient information, etc., in addition to image data during an image acquisition by the x-ray machine with respect to a patient. The example x-ray machine serves as a translator to capture, format, and interpret information from a plurality of sources (e.g., targeted, generated, ambient, etc.). In certain examples, the x-ray device includes an artificial intelligence model (e.g., a machine learning model, a deep learning model, etc.) to evaluate, format, etc., captured information. The artificial intelligence model can correlate multiple types of information (e.g., image data and vitals information, etc.), for example. The artificial intelligence model can predict a presence of a disease or other condition by processing multiple types of information (e.g., image data and vitals information, etc.), for example. The artificial intelligence model can identify a trend in a disease or other condition (e.g., improving, worsening, etc.) by processing multiple types of information (e.g., image data and vitals information, etc.), for example.

Example methods and apparatus disclosed herein facilitate the aggregating of vital information into an x-ray image to increase accuracy of patient diagnosis and reduce the time it takes to read an x-ray image. For example, techniques disclosed herein facilitate capturing vital information via a video capturing device and/or audio device during an x-ray procedure, then embedding the vital information into the x-ray image. By using a video capturing device to capture the display of the vital monitor and an audio device to record vitals dictated by a health care specialist during the x-ray procedure, a health care provider can accomplish patient vital data collection in a vendor neutral way (e.g., a health care provider does not need to use a specific type of x-ray machine to accomplish embedding vital information into an x-ray image).

By providing imaging services via a mobile or portable x-ray imaging device, clinicians can provide more on-the-spot examination and diagnosis without having to transport the patient to a separate room or imaging facility. By also being able to capture vitals in real time with the imaging data, the system can provide a more comprehensive view of the patient's condition and overall health at the moment of data acquisition trigger. Additionally, if captured image and/or vitals data is of low quality and/or if the captured image and/or vitals data indicates an issue that warrants further review, subsequent image and/or vitals data can be captured again on the spot while the mobile imaging device is still with the patient, rather than waiting to analyze until the patient is back in his/her room (or at home) and then needs to be rescheduled for another visit.

In addition to capturing vitals data to merge with imaging data, certain examples integrate patient history (e.g., patient demographic data, patient exam data, prior patient vitals data, prior patient imaging data, etc.) to provide context to help determine whether the patient is stage, improving in condition, worsening in condition, etc. Wired and/or wireless communication channel(s) can be used to capture patient vitals data, patient imaging data, patient history and/or other context information, etc. Vitals data, patient history information, etc., can be tagged and embedded (and/or otherwise incorporated) in the image data to form a composite image to aid in patient diagnosis, treatment, etc. (and/or patient population diagnosis, treatment, etc.), for example. The tagged, embedded information can be used by one or more artificial intelligence models to automatically process patient image data, predict a patient outcome (e.g., presence of a disease/condition, condition improving, condition worsening, etc.).

The combination of tagged data associated with the patient helps the artificial intelligence model process and correlate to triage, alert, and provide predictive and/or prescriptive analytics, for example. As such, one or more artificial intelligence models can generate and/or support clinical diagnosis based on an accumulation of clinical vitals data (e.g., body temperature, pulse rate, respiration rate, blood pressure, oxygen level, etc.), patient history, imaging data (e.g., x-ray images, ultrasound images, computed tomography images, magnetic resonance images, nuclear medicine images, etc.), etc. The collection of data enables diagnosis decisions, treatment decisions, patient/population management decisions, etc.

In examples disclosed herein, a health care provider facility is a place where medical care is provided to a patient in need. Examples of a health care provider include a hospital, dental office, clinic, or any other location that specializes in diagnostic procedures.

In examples disclosed herein, a health care specialist (specialist) is a medical professional who diagnosis and treats a patient's medical condition. Examples of a health care specialist include a Radiologist, a Surgeon, a Pediatrician, an Oncologist, an Obstetrician, etc.

In examples disclosed herein, the terms vital or vitals (also referred to herein as vital information or vitals information) represents a number of a unit of measure and/or other value that provides critical information about a patient's state of health. Specifically, these numbers can identify the existence of an acute medical condition, can provide support for a diagnosis by a health care specialist, can rapidly quantify the magnitude of illness and how a body is coping with resultant physiologic stress, or they can be a marker indicating a chronic disease state, for example. In some examples, a vital number can represent heart rate, blood pressure, oxygen saturation, body temperature, respiratory rate, etc. The numbers of each vital representation have different measured values. For example, heart rate is measured by beats per minute (bpm), blood pressure is measured by millimeters of mercury (mm Hg), respiratory rate is measured by breaths per minute (different than beats per minute, bpm), and oxygen saturation is measured by a percentage of how much oxygen the blood is carrying compared to the maximum amount the blood is capable of carrying. In contrast, a standard method to retrieve vitals data may be via a health care specialist reading the values displayed on a vitals monitor and taking a note in a book or typing them into an electronic medical record (EMR) using a computer.

In examples disclosed herein, the term patient medical data is private data that corresponds to demographic data, past and present medical information, and family history of a patient. For example, patient A is a female 32 years of age, weighs 130 pounds, lives in a small town of Indiana, has two children, obtained chicken pox at the age of 6, has had surgery on a broken ankle, is taking medication of type A, type B, and type C, and has a mother and grandmother who both had breast cancer. Patient medical data is located in a secure database at health care provider facilities and is provided only to health care specialists.

A variety of patient medical data can be combined with image data to drive detection/diagnosis of a disease or condition. For example, patient vitals and imaging data are collected at an x-ray system and associated patient monitor. If the patient's oxygen level has been consistently between 94-96% for one week in an intensive care unit (ICU) and then drops to 91% one day, the patient's oxygen level may still be considered a "normal" level (e.g., since it is greater than 90%, etc.). However, the patient's oxygen level still exhibits a marked change based on his/her own history (e.g., from 94-96% down to 91%, etc.). When paired with a suspicious imaging finding, a machine learning model (e.g., a convolutional neural network (CNN), a recurrent neural network (RNN), other neural network, etc.) and/or other artificial intelligence model can generate a score indicative of a pneumothorax. Captured vitals data can be analyzed (e.g., compared to prior patient vitals data, etc.) by the same and/or an additional artificial intelligence network. A combination of patient oxygen level, patient image data, and patient vitals data comparison provides a strong indicator of a collapsed lung, for example.

In other examples, endotracheal (ET) tube position, nasogastric (NG) tube position, free air, etc., can be identified from a combination of image data, patient vitals data, and patient history information. A diagnosis (e.g., pneumothorax, acute respiratory distress syndrome (ARDS), etc.), treatment, and/or other follow-up can be determined using one or more artificial intelligence models processing the combination of available information.

Typically, patient vitals are specifically taken and at a different timestamp than when the imaging data (e.g., chest x-ray, etc.) was obtained. Further, the radiologist does not look at an electronic medical record (EMR) because he or she is looking at data in a picture archiving and communication system (PACS). To remedy these problems, certain examples enable a snapshot of patient clinical signals to be captured at a first moment in time along with imaging data captured at the same moment in time. The imaging system (e.g., an x-ray imaging device, computed tomography imaging scanner, ultrasound scanner, magnetic resonance imager, etc.) captures the image, and vitals data can be captured by a monitor and wirelessly transmitted at the same time in correlation with the image data. The combined set of image plus vitals data can be stored in the PACS, EMR, etc., and provided to the radiologist, artificial intelligence model, etc. The imaging device can serve as the wireless and/or wired interceptor or gathering point to capture data according to a plurality of formats via a plurality of communication standards and correlate the information. The data in various formats can be maintained and processed in its native format (e.g., DICOM, HL7, FHIR, etc.), converted to a single format, etc. As such, the imaging device can be positioned in the emergency room, the operating room, the intensive care unit, etc., and used to capture, correlate, analyze, and store both imaging and non-imaging patient data to drive improved outcomes.

Figure 2A:
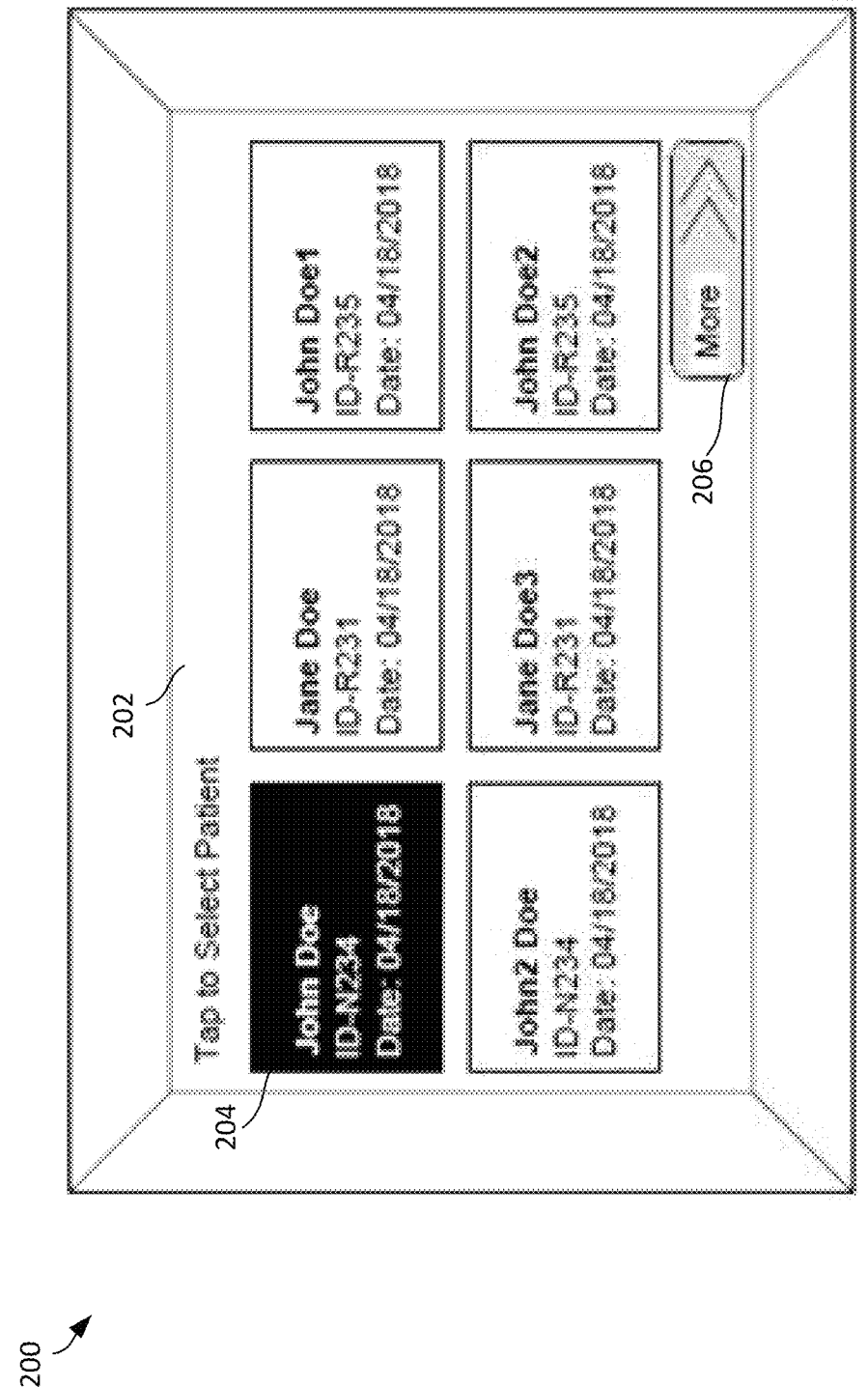
FIG. 2A is an example user interface display to prompt a user to select a patient associated with the x-ray.
Figure 2B:
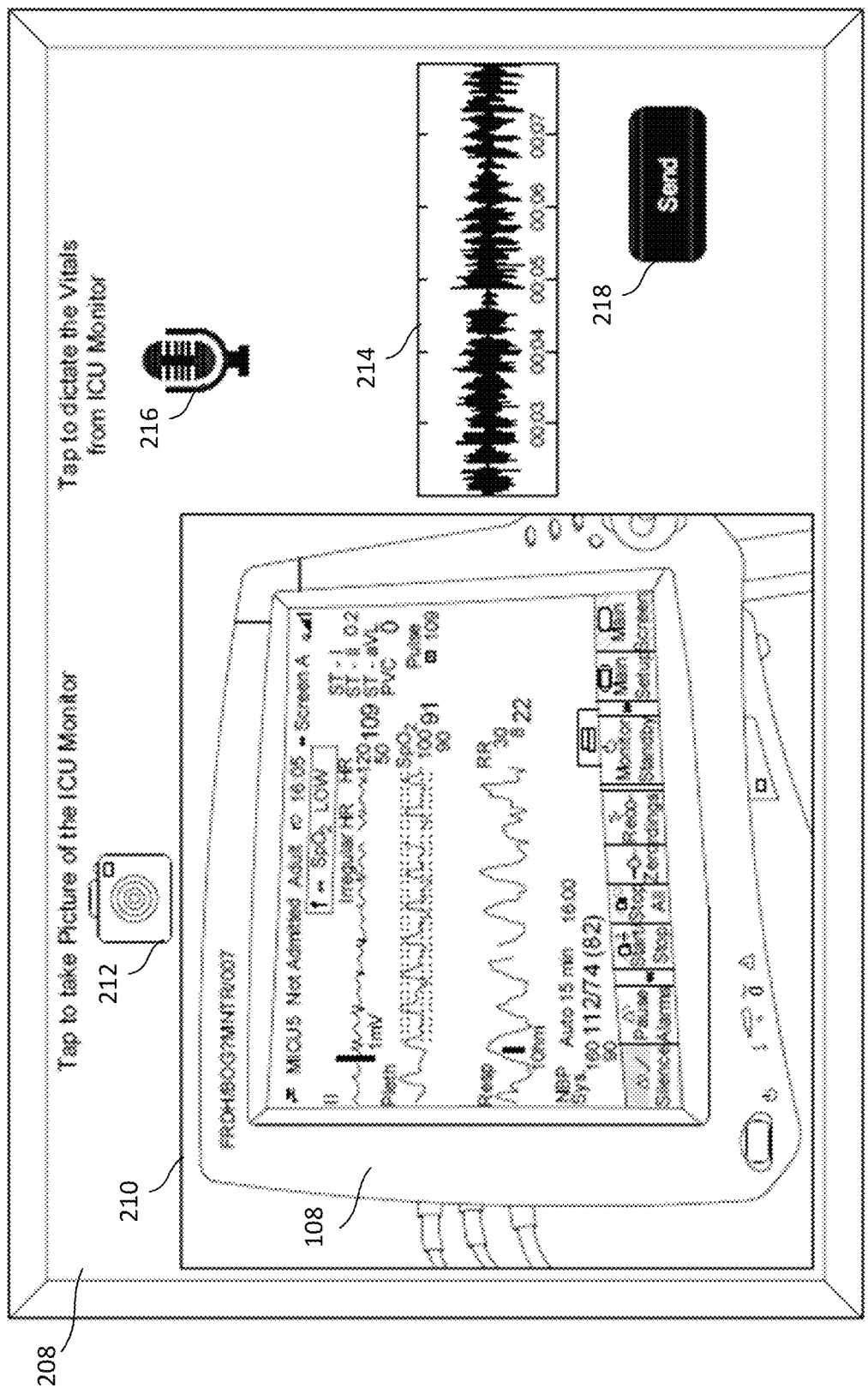
FIG. 2B is an example user interface display to prompt a user to select the type of vital capturing system.
Figure 3A:
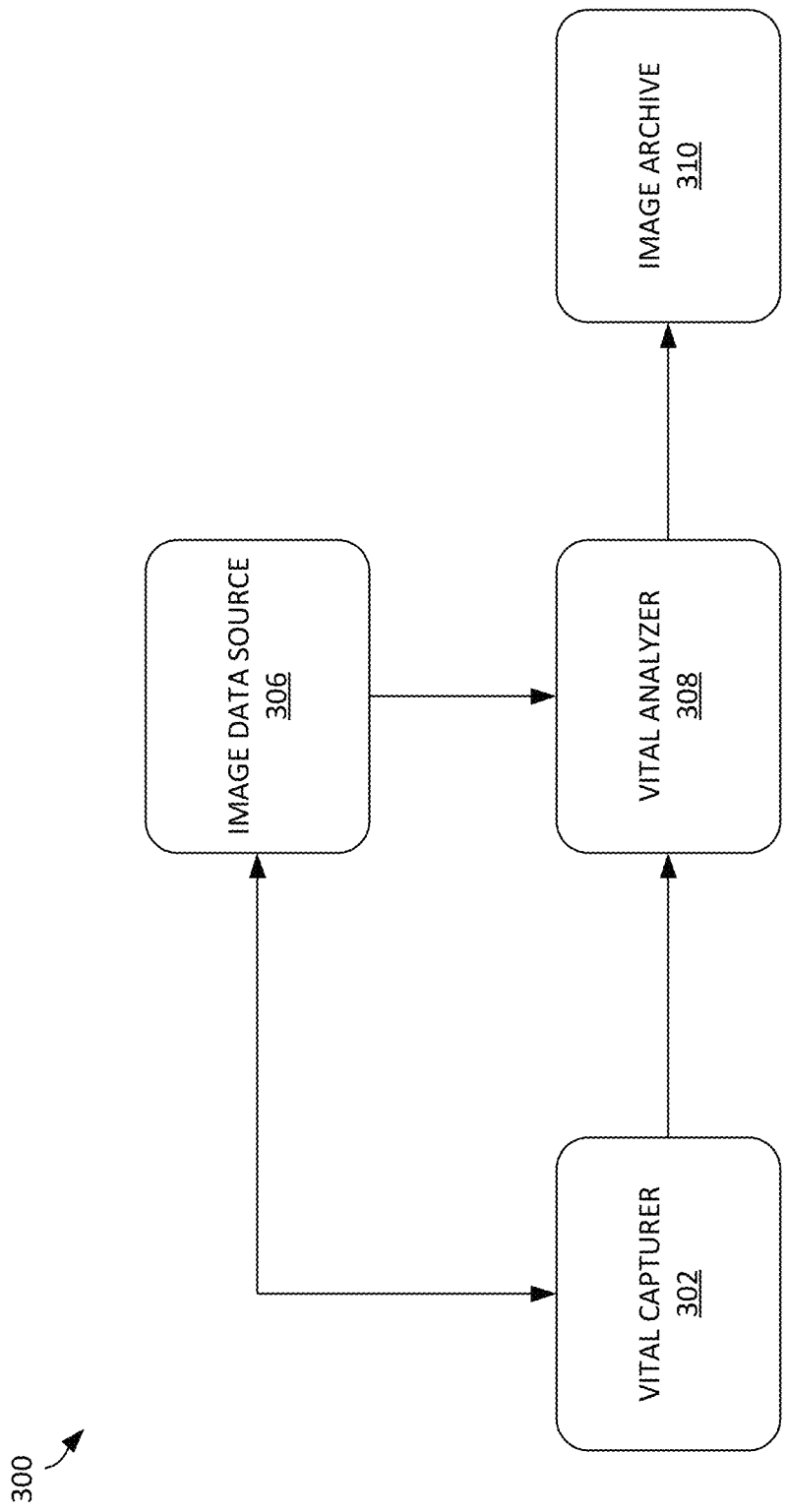
FIG. 3A is an example apparatus to capture, process, and store vitals of a patient undergoing an x-ray procedure.

FIGS. 1, 2A, and 2B illustrate an example environment including a mobile apparatus to capture imaging and vitals information of a patient during an imaging procedure. FIGS. 2A and 2B illustrate the example displays of the example user interface 200 of FIG. 1. FIGS. 3 and 4 illustrate the example system that employs the environment of FIG. 1 to capture vital information of a patient during an x-ray procedure and produce an embedded x-ray image for a health care specialist. In FIG. 3A, the example system is shown as a block diagram of each pertinent component of the system. In FIG. 4, the example system represents the flow of data inside the example vital analyzer 208 of FIG. 3A.

FIG. 1 is an example environment 100 representative of a health care provider room wherein the vital capturing device and the x-ray device are in use to capture patient vitals during an x-ray imaging procedure. The example environment 100 includes an example health care specialist 102, an example sound wave 104, an example photo capturing device 106, an example audio receiving device 108, an example image data source 306, an example vitals monitor 112, an example user interface 200, and an example aggregate system 300.

In the illustrated example, the environment 100 includes the specialist 102 to take an x-ray image of a patient in critical condition. For example, the specialist 102 positions the x-ray device at a location that would capture the area of the body which the patient may be in pain, have discomfort, show a lump or bruise, etc. The specialist 102 also operates the example vital monitor 112, and the example aggregate system 200 which includes the video capturing device 106, the example user interface 200, and the example audio receiving device 108. In the example environment 100, the specialist 102 is trained to operate the example aggregate system 200.

In the illustrated example, the environment 100 includes a representation of a sound wave 104 to dictate vitals to the audio receiving device 108 of the aggregate system 200. For example, the specialist 102 is viewing the display shown on the vital monitor 112 and reading the vitals out loud (e.g., dictating the vitals), generating sound waves 104 for the audio receiving device 108. Additionally or alternatively, the sound wave 104 may be a sound wave 104 from a speaker or other entity or an audio signal corresponding to a sound wave (e.g., an electrocardiogram (ECG), ultrasound, dictation playback and/or other generated computer speech, etc.).

In the illustrated example, the environment 100 include a video capturing device 106 to capture visual vital information of the patient from the vital monitor 112 during an x-ray procedure. For example, when the x-ray device is taking pictures of the patient, the video capturing device 106 is taking multiple frames of the vital monitor 112 to monitor the patient's vitals. The example video capturing device 106 is a 360 degree rotatable camera that can adjust its position according to the location of the vital monitor 112. The example video capturing device 106 may be coupled to the image data source 306 at any location.

In the illustrated example, the environment 100 is provided with an audio receiving device 108 to capture audible vital information of the patient during the x-ray procedure. For example, the audio receiving device 108 can receive the sound wave 104 dictated by the specialist 102 and convert the sound wave 104 into electrical energy (e.g., an audio signal). In the illustrated example, the audio receiving device 108 is a microphone that may be coupled to or integrated into the example image data source 306. For example, the audio receiving device 108 may be external or internal, the external device seen as protruding or sticking out of the image data source, the internal device not seen by a user.

In the illustrated example, the environment 100 is provided with the image data source 306 to take an x-ray image of a patient. The example image data source 306 is a mobile device with integrated computed radiography (CR) plates that can be relocated throughout a health care provider facility for accessibility and quicker results. In some examples, computed radiography (CR) plates are a digital replacement of conventional x-ray film radiography which utilizes a flexible phosphor imaging plate to capture a digital image instead of conventional photographic film. For example, the image data source 306 may expose an imaging plate to x-rays, digitize the plate by a laser scanner, remove the x-rays off the plate, and then display the digitized image on the example user interface 200. The image data source 306 is mobile and may be moved from one ICU to another ICU, or from one operating room (OR) to another OR, depending on where it is needed. Additionally or alternatively, the example image data source 306 may be a conventional x-ray device that utilizes a film to capture the x-ray image, a stationary x-ray device, or any other type of radiography device that produces an output image of the internal structures of a patient's body.

The example image data source 306 also is to process and transform a received x-ray image from the to a readable format. The example image data source 306 can be a digital imaging and communications in medicine (DICOM) compliant system that stores, produces, displays, sends, queries, processes, retrieves, and prints the x-ray image. As used herein, DICOM is the international standard that defines the formats for medical images that can be exchanged with the data and quality necessary for health care use. For example, when an x-ray image is captured of a patient's broken elbow, the image data source 306 may add a header on the image that includes the time the image was taken, the date, the location, etc.

In the illustrated example, the environment 100 is provided with the vital monitor 112 to display the vitals of a patient. The example vital monitor 112 receives information in real time from sensors attached to a patient corresponding to heart rate, blood pressure, etc., and displays the received information on the vital monitor 112. The example vital monitor 112 can be a mobile device which can be relocated throughout a health care provider facility.

In the illustrated example, the environment 100 is provided with a user interface 200 of the example aggregate system 300 to prompt a user (specialist) to load a patient record to initiate the x-ray imaging procedure. For example, selecting a patient record provides a trigger to activate the aggregate system 300. To select the patient record, the user utilizes the example user interface 200 which can be a liquid crystal display (LCD) mounted to the image data source 306 but may be any other type of display. The display can be a touch screen display, such as a tablet computer, custom interface display, etc. In some examples, the user interface 200 may also be integrated into the image data source (e.g., the body of the x-ray device has a display built into it, and no mounting has taken place).

In the illustrated example, the environment 100 is provided with the aggregate system 300 to combine the example video capturing device 106, the example audio receiving device 108, the example image data source 306, and the example user interface to facilitate the aggregating of the received data from each entity, into one image. For example, the aggregate system 200 may receive a sound wave 104 from a specialist 102 containing information about patient vitals, and the image data source 306 may produce an x-ray image on an x-ray plate. The received sound wave 104 and the produced x-ray image on a plate may be processed together by an imaging technique such as DICOM.

FIGS. 2A and 2B are example user interface 200 displays representative of what a specialist 102 will visually see during the process of taking an x-ray image of a patient and capturing their vitals. The example user interface 200 includes an example patient selection display 202, an example patient information box 204, an example "more" interactive box 206, an example vital capturing option display 208, an example captured image 210, an example interactive camera icon 212, the example vital monitor 112, an example audio signal display 214, an example interactive microphone icon 216, and an example "send" interactive box 218.

In some examples, the example system 300 can be implemented without the interface 200 of FIG. 2A. For example, rather than presenting the user interface 200 to the specialist 102 to prompt a user to select a patient associated with the x-ray, the example aggregate system 300 can receive a selection prior to initiating the x-ray procedure.

In some examples, the example system 300 can be implemented without the interface 200 of FIG. 2B. For example, the aggregate system 300 can include a voice query and natural-language user interface technology to enable dictation of audio vitals. In other examples, the aggregate system 300 can include an automatic video and/or photo capturing device that utilizes machine learning to recognize an image and capture a frame of the image without user input.

In the illustrated example, the user interface 200 is provided with the patient selection display 202 to provide a visualizing and interactive option to a health care specialist to select a patient that is undergoing an x-ray procedure. In some examples, the patient selection display 202 is an LCD, a touch sensitive interactive display, or any other visual display device with which a user can interact.

In the illustrated example, the user interface 200 is provided with an example patient information box 204 to represent and identify a patient with which the x-ray image data and captured vitals data will be associated. For example, patient information box 204 includes the patient name, the patient identifier, and the date the patient is undergoing an x-ray procedure. In some examples, the patient information box 204 may display other information such as patient date of birth, patient age, an image of the patient, etc. The information included with the patient information box 204 assists a health care specialist 102 in the process of selecting a patient. The patient selection display 202 can include a plurality of patient information boxes 204.

In the illustrated example, the user interface 200 is provided with a "more" interactive box 206 to provide an option to a health care specialist 102 to view more patient information boxes 204. For example, a specialist 102 can touch, click, press, push, or use any other interactive method to select the interactive box 206. In some examples, if the "more" interactive box 206 is selected, a new display screen may show a list of new patient information boxes that were not seen on the patient selection display 202.

In the illustrated example, the user interface 200 is provided with a vital capturing option display 208 to provide visualizing and interactive options to a specialist 102 to select a method to capture a patient's vitals during an x-ray procedure. The display can be an LCD display, a touch sensitive interactive display, or any other visual display device in which a user can interact with.

In the illustrated example, the user interface 200 is provided with an example captured image 210 of the vital monitor 112 to provide a visual to the specialist 102 of the patient's vitals during an x-ray procedure. In some examples, the captured image 210 is in real time, a previous image taken, or a pre-defined and illustrated image.

In the illustrated example, the user interface 200 is provided with an example interactive camera icon 212 to provide the aggregate system 300 with an instruction to activate the video capturing device 106. For example, a specialist 102 can touch, click, press, push, or use any other interactive method to select the interactive camera icon 212 in which the selection sends data via a network to the aggregate device 300. The example aggregate device 300 may be electrically coupled to the example video capturing device 106 and may therefore activate it.

In the illustrated example, the user interface 200 includes an example audio signal display 214 to visually represent a received audio signal corresponding to an example sound wave 104 from the specialist 102 recorded by the example audio receiving device 108. For example, the audio signal display 214 can be a sine wave, a square wave, a distorted wave, or any other type of wave/s that represent the audio signal corresponding to an example sound wave 104. In some examples, the audio signal display 214 can be time stamped. In other examples, the audio signal display 214 can be in real time, a display from a previous patient, or a pre-defined display.

In the illustrated example, the user interface 200 includes the example interactive microphone icon 216 to provide the aggregate system 300 with an instruction to activate the audio receiving device 108. For example, a specialist 102 can touch, click, press, push, or use any other interactive method to select the interactive microphone icon 216 in which the selection sends data via a network to the aggregate device 300. The example aggregate device 300 can be electrically coupled to the example audio receiving device 108 and may therefore activate it.

In the illustrated example, the user interface 200 includes the example "send" interactive box 218 to provide an instruction to the aggregate system 300 to send all received data (e.g., the captured video frames and audio signals) to an example vital analyzer 308 of FIG. 3A. For example, the "send" interactive box 218 is selected by the specialist 102 after an x-ray procedure has taken place and all vital data that a specialist 102 may need has been captured (e.g., heart rate/ECG data, voice dictation, etc.).

While an example implementation of the user interface 200 of FIG. 1 is illustrated in FIGS. 2A and 2B, one or more of the elements, processes and/or devices illustrated in FIGS. 2A and 2B may be combined, divided, re-arranged, omitted, eliminated and/or implemented in any other way. Further, the example patient selection display 202, the example patient information box 204, the example "more" interactive box 206, the example vital capturing option display 208, the example captured image 210, the example interactive camera icon 212, the example vital monitor 112, the example audio signal display 214, the example interactive microphone icon 216, the example "send" interactive box 218 and/or, more generally, the example user interface 200 of FIG. 1 may be implemented by hardware, software, firmware and/or any combination of hardware, software and/or firmware. Thus, for example, any of the example patient selection display 202, the example patient information box 204, the example "more" interactive box 206, the example vital capturing option display 208, the example captured image 210, the example interactive camera icon 212, the example vital monitor 112, the example audio signal display 214, the example interactive microphone icon 216, the example "send" interactive box 218 and/or, more generally, the example user interface 200 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example patient selection display 202, the example patient information box 204, the example "more" interactive box 206, the example vital capturing option display 208, the example captured image 210, the example interactive camera icon 212, the example vital monitor 112, the example audio signal display 214, the example interactive microphone icon 216, the example "send" interactive box 218 is/are hereby expressly defined to include a non-transitory computer readable storage device or storage disk such as a memory, a digital versatile disk (DVD), a compact disk (CD), a Blu-ray disk, etc. including the software and/or firmware. Further still, the example user interface 200 of FIG. 1 may include one or more elements, processes and/or devices in addition to, or instead of, those illustrated in FIGS. 2A and 2B, and/or may include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

FIG. 3A is an example apparatus to capture, process, and store vitals of a patient undergoing an x-ray procedure. The example apparatus is provided with an example vital capturer 302, an example image data source 306, and example vital analyzer 308, and an example image archive 310.

The illustrated apparatus of FIG. 3A includes an example vital capturer 302 to capture vitals of a patient in real time during an x-ray procedure. The example vital capturer 302 includes the example video capturing device 106 and the example audio receiving device 108 of FIG. 1. For example, the video capturing device 106 utilizes a lens positioned towards the example vital monitor 112 and, once activated, the video capturing device 106 captures image and/or video frames of the image the lens is positioned towards (e.g., the vital monitor 112), and store them. In some examples, the audio receiving device 108 may receive a sound wave 104 from the example specialist 102 and convert the sound wave 104 into an audio signal that may be processed by the example vital analyzer 308.

The illustrated apparatus of FIG. 3A includes an example image data source 306 to take an x-ray image of a patient with a medical condition. In examples described above, the x-ray device produces an image of the internal structure of a patient in order to allow a specialist 102 to review the medical condition of a patient and diagnose them properly.

In some examples, the vital capturer 302 and the image data source 306 are operated simultaneously to capture patient vitals and patient internal structures in real time. Additionally or alternatively, the vital capturer 302 can operate at a different time than the image data source 306 and the image data source 306 can operate at a different time than the vital capturer 302. The example vital capturer 302 and the example image data source 306 can be controlled or operated by the example user interface 200, the example specialist 102, or any other type of user that may need to interact with the entities.

In the illustrated example, the apparatus of FIG. 3A includes a vital analyzer 308 to process vital data, transform it to a readable format, and aggregate it with an x-ray image. The example vital analyzer 308 can be coupled to the aggregate system via wireless communications or a wired connection. The example vital analyzer 308 can also receive data via a network, and edge device, or a cloud device. For example, the vital analyzer 308 can be located in a different health care provider facility room than the example aggregate system 300 and may, therefore, receive data via an edge device.

In the illustrated example, the apparatus of FIG. 3A includes an image archive 310 to store and process the x-ray image received from the example vital analyzer 308. The example image archive 310 is a picture archiving and communications system (PACS). As used herein, a PACS is a medical imaging technology used to securely store and digitally transmit electronic images and clinically-relevant reports. The example image archive 310 receives an aggregate x-ray image of a patient and provides the image, via a network, to a quality assurance device. The quality assurance device determines the information provided in the aggregate x-ray image (e.g., the DICOM header) is correct. For example, the quality assurance device can scan the information in the DICOM header for inconsistencies of the patient information. When the inconsistencies have been determined and corrected, the aggregate x-ray image is provided to an archive for storage. Additionally, the aggregate x-ray image can be stored in many archives in different locations for a means of recovering the image in case of an error or disaster at the health care provider facility. Additionally or alternatively, the example image archive 310 can be a file server stored in a health care provider facility, can be a database is located in the aggregate system 300, or any other storage entity that would facilitate securing and filing an image.

Figure 3B:
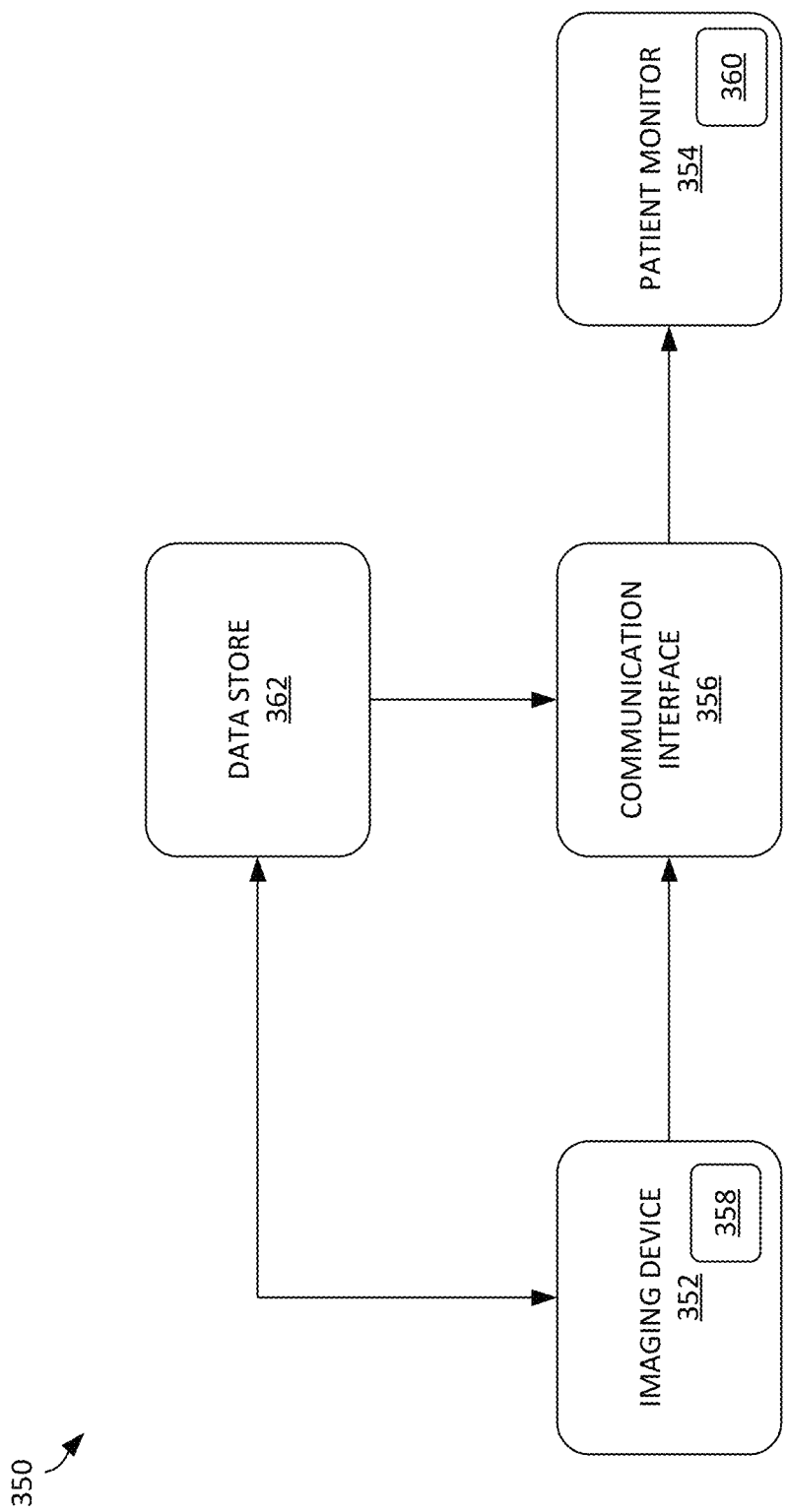
FIG. 3B is another example apparatus to capture, process, and store patient imaging and non-imaging information at a point of care during a procedure.
Figure 4:
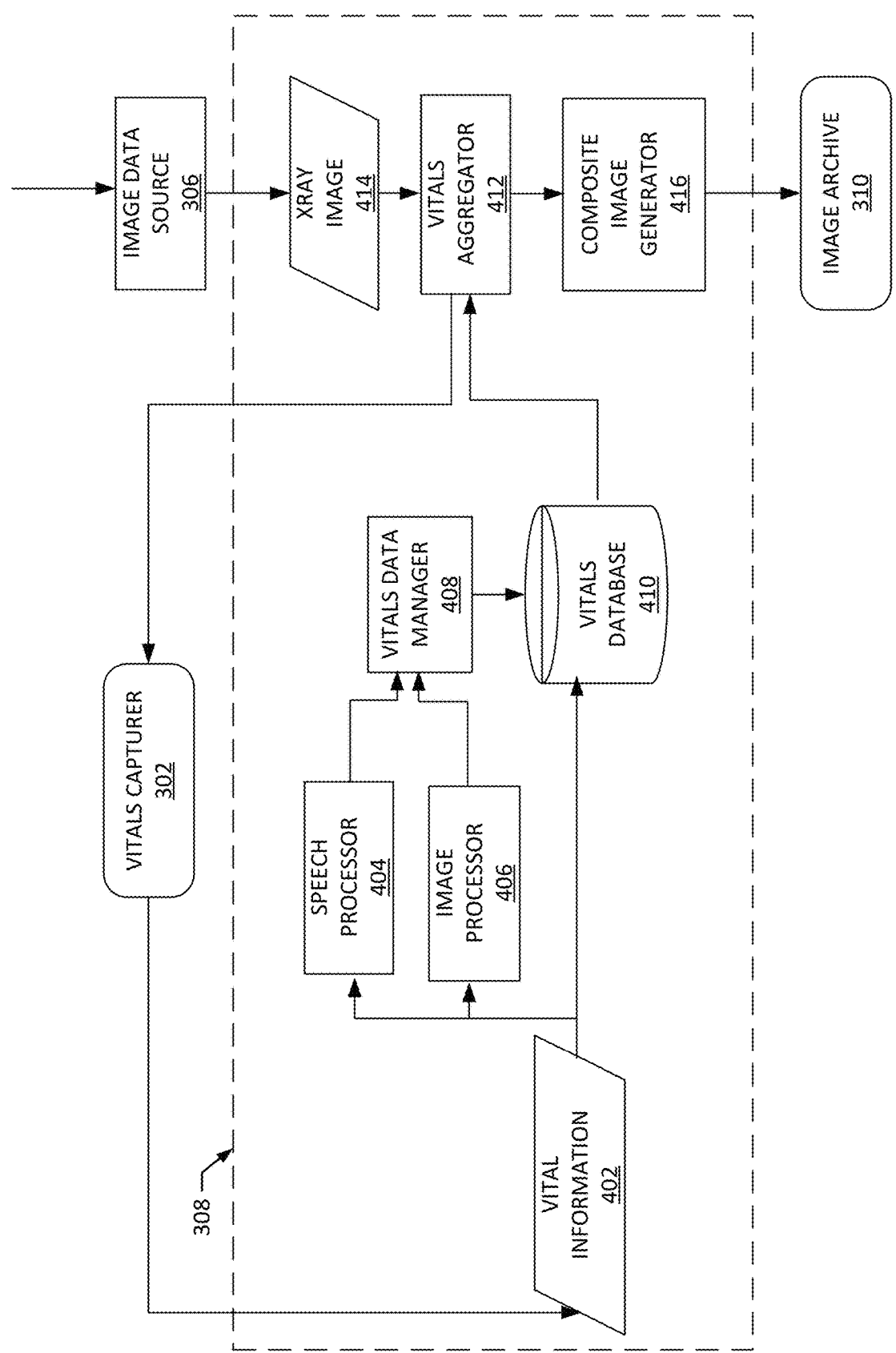
FIG. 4 is an example apparatus representative of the vital analyzer of FIG. 3A to analyze the captured vitals.

FIG. 3B illustrates an alternative or additional implementation of the example system 300 to capture image and/or other patient information. FIG. 3B shows a system 350 including an imaging device 352 (e.g., the image data source 306), a patient monitor system 354, and a communication interface 356 to gather and exchange information between the imaging device 352 and the patient monitor 354. In the example system 350, one or both of the imaging device 352 and the patient monitor 354 can include an artificial intelligence (AI) model 358, 360. In certain examples, the AI model 358 is included in the imaging device 352, but, in other example, both the imaging device 352 and the patient monitor 354 include AI models 358, 360. Data can be stored in a data store 362 (e.g., an EMR, a PACS, an enterprise archive, a vendor neutral archive, another memory or data storage, etc.), which may or may not have its own AI model, for example.

In operation, the imaging device 352 (e.g., an x-ray imaging device, a computed tomography imaging device, an ultrasound imaging device, a magnetic resonance imaging device, a nuclear imaging device, etc.) captures image data, and the patient monitor 354 (e.g., a microphone, a camera, a heart monitor, a pulsometer, a thermometer, another sensor, etc.) captures patient vitals data to be shared with the imaging device 352 via the communication interface (e.g., Wi-Fi, Bluetooth, NFC, USB, ethernet, etc.) 356. The communication interface 356 is a wired and/or wireless communication conduit or connection that can be formed via a physical wire (or set of wires) and/or wirelessly between an imaging device 352 receiver and a patient monitor 354 transmitter, for example. In some examples, communication is uni-directional captured from the patient monitor 354 by the imaging device 352. In other examples, communication is bi-directional between the imaging device 352 and the patient monitor 354.

The AI model 358 on the imaging device 352 can be used to extract information from a picture taken by a camera showing the patient vitals information on a display associated with the patient monitor 354 (e.g., using optical recognition of characters/numbers representing patient vitals, etc.), for example. The Alternatively or additionally, the AI model 358 can be used for classification of pictures/icons showing or related to heart rate, temperature, oxygen saturation, etc., for example. In certain examples, the AI model 358 (e.g., a trained RNN, CNN, etc.) can be used for audio processing of recorded patient data using speech recognition, etc. In certain examples, image and vital data can be combined into training, testing, and deployed usage of the AI model 358 to predict and/or detect clinical outcomes such as pneumothorax, ARDS, improper tube placement, etc. An output of the AI model(s) 358, 360 can be stored in the data store 362 and used by data store AI and/or provided to another system, or kept by the imaging system 352 to track trends in vitals based on readings for previous patient exams, highlight vitals trends on the image (e.g., key trends highlighted on an x-ray image, etc.), etc.

FIG. 4 illustrates an example implementation of the vital analyzer 308 to process, combine, and store an x-ray image with captured vital data. The example vital analyzer 308 includes an example speech processor 404, an example image processor 406, an example vitals data manager 408, and example vitals database 410, an example vitals aggregator 412, and an example composite image generator 416. Additionally or alternatively, the apparatus of FIG. 4 includes the example image data source 306 and the example image archive 310.

The example vital analyzer 308 includes an example speech processor 404 to convert speech to text. The example speech processor 404 converts speech to text by first converting the sound wave 104 into a digital signal via an analog to digital converter (ADC) by sampling the sound wave 104. As used herein, sampling means taking precise measurements of the sound wave 104 at frequent intervals and storing the samples in a memory for future retrieval. The speech processor 404 then filters the digital signal to remove unwanted noise such as white noise, ambient noise, background noise, etc. The example speech processor 404 may then normalize the sound (e.g., adjust it to a constant volume level) by a low pass filter, a high pass filter, a band pass filter, etc. Next, the normalized digital signal is divided into small segments as short as a few thousandths of a second and the segments are matched to known phonemes in the appropriate language. As used herein, a phoneme is the smallest element of a language such as a representation of the sounds we make and put together to form meaningful expressions. In the English language, there are about 40 phonemes, while other languages may have more or less. After matching the segments to the phonemes, the example speech processor 404 examines the phonemes in the context of the other phonemes around them and runs a contextual phoneme plot through a statistical model and compares them to a large library of known words, phrases, and sentences. In this example, the known phrases and sentences may include medical terms used predominantly by health care specialists. The example speech processor 404 then determines what the specialist 102 was saying and provides an output either as text, a computer command, etc. The example speech processor 404 provides the output to the example vitals data manager 408.

The example vital analyzer 308 includes an image processor 406 to convert a video into computer readable text. The example image processor uses video optical character recognition to achieve conversion. The video is taken by the example video capturing device 106 where the video is segmented into a sequence of frames. As used herein, a frame is one of the many still images which compose a complete moving picture. The video capturing device 106 is focused on the example vital monitor 112 and therefore captures a video of what is displayed on the example vital monitor 112 screen. The example image processor 406 scans a frame for characters, compares the characters of the frame to shapes in a database, and determines which characters the video capturing device 106 captured, then converts the character to text by changing the pixel values to 1's and 0's. The example image processor 406 provides the text to the example vitals data manager 408 to be further analyzed. Additionally or alternatively, the example image processor 406 can use a convolutional neural network, linear filtering, anisotropic diffusion, independent component analysis, etc.

The example vital analyzer 308 includes the vitals data manager 408 to receive the captured visual vitals information and the captured audible vitals information from the vitals capturer 306 and tag the captured vitals information with an identifier of a patient to form tagged vitals information. The vitals data manager 408 can determine what vital data is pertinent to the patient and the x-ray image associated with the patient. For example, the vitals data manager 408 can receive a plurality of random strings of text from the example image processor 406 and/or speech processor 404 and must determine what strings include metadata corresponding to the patient.

The example vital analyzer 308 includes the example vitals database 410 to store vital information 402 and vitals data received from the vitals data manager 408. In some examples, vitals database 410 can rearrange and relocate received data depending on if it is an image or an audio signal.

The example vital analyzer 308 includes the example vitals aggregator 412 to receive the tagged vitals information and the x-ray image 414 associated with the patient and organize the tagged vitals information with the x-ray image 414 to form a composite image. For example, the vitals aggregator 412 can combine a vital information with an x-ray image. The example image data source 306 provides an x-ray image 414 to the example vitals aggregator and the example vitals aggregator 414 determines the patient corresponding to the x-ray image 414 by the metadata in the header of the x-ray image 414. The example vitals aggregator 412 receives a notification and/or a trigger from the example vitals capturer 302 to aggregate the vitals information and the x-ray image data and is further provided with the vitals information corresponding to the patient of the x-ray image 414.

When the vitals aggregator 412 aggregates the vitals data and the x-ray image data, the example vitals aggregator 412 adds the vitals data to the DICOM header of the example x-ray image 414. Additionally or alternatively, the example vitals aggregator 414 can add the vital information to a footer of the example x-ray image 414, to the side margins of the example x-ray image 414, to an encapsulated portable document format (PDF) image attached to the x-ray image, or anywhere else on the x-ray image 414 that does not hinder the view of the patient's internal structure represented in the image 414.

In some examples, the vitals aggregator 412 analyzes the composite image to determine if the visual vital information and/or the audible vital information matches the x-ray image data. For example, the vitals aggregator 412 can implement a machine learning model to analyze the x-ray image data to determine that the x-ray image 414 includes a heart. The machine learning model analyzes the vitals information to determine if the vitals include an electrocardiogram (e.g., ECG), which measures electrical activity of a heart. If the vitals information does not include an ECG, the vitals aggregator 412 sends a trigger and/or prompts a warning to the user interface informing the user that an ECG was not captured by the vitals capturer 302 and requesting an instruction to confirm the user does not want to recapture the vitals information. If the user requests to recapture, then the vitals aggregator 412 sends a trigger to the vitals capturer 302 for a new vitals data acquisition trigger. If the user requests to not recapture, the vitals aggregator 412 continues to aggregate the vitals information and the x-ray image data. Additionally, the vitals aggregator 412 can utilize a convolutional neural network, a statistical probability based model, or other prediction model to compare the x-ray image data and vitals information determine if there is not a match or correlation between the two, for example. Thus, the vitals aggregator 412 can confirm that the captured vitals information matches and/or corresponds to the acquired image data (e.g., is from the same patient, relates to the same anatomy or condition, has allowed values, etc.), and can trigger an alert and/or otherwise prompt a recapture of different and/or further vitals with respect to the patient and the image data, for example.

The example vital analyzer 308 includes the example composite image generator 416 to embed tagged vitals information with an x-ray image to form a composite image. For example, the composite image x-ray generator 416 may be a device that associates vitals data with pertinent segments of the x-ray image data, creates a composite image file, overlays the vitals data on the pertinent segments of the x-ray image data in the composite image file, and embeds the vitals data in the header of the composite image file. The composite image file is provided to the image archive 310. For example, the image archive 310 is a PACS viewer, where a healthcare specialist can retrieve the composite image from the example composite image generator 416 and view it on a device or have it printed to view as a physical copy.

Figure 5:
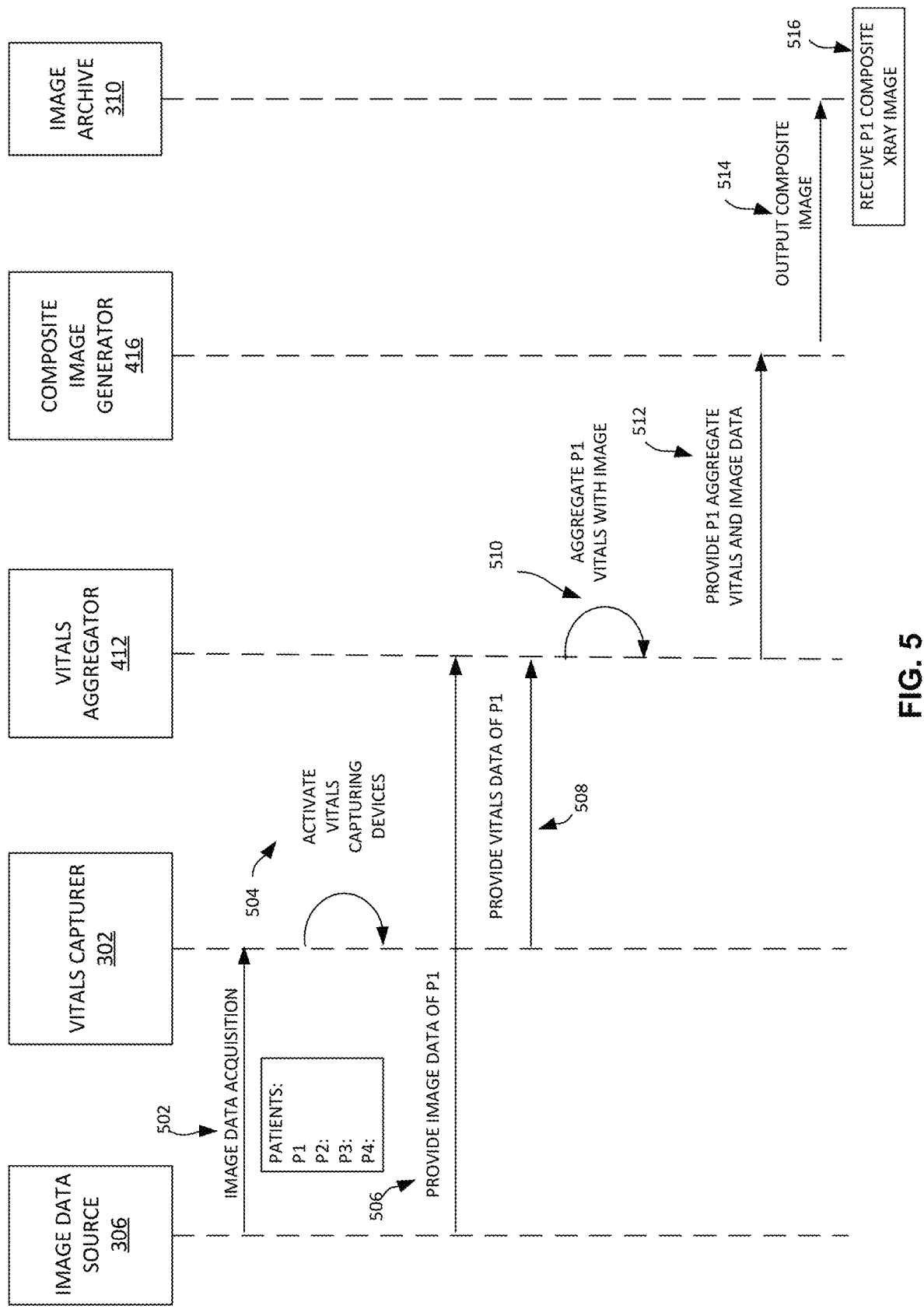
FIGS. 5 and 6 are example workflow diagrams to show the relationship between the data flow of each ER block.
Figure 6:
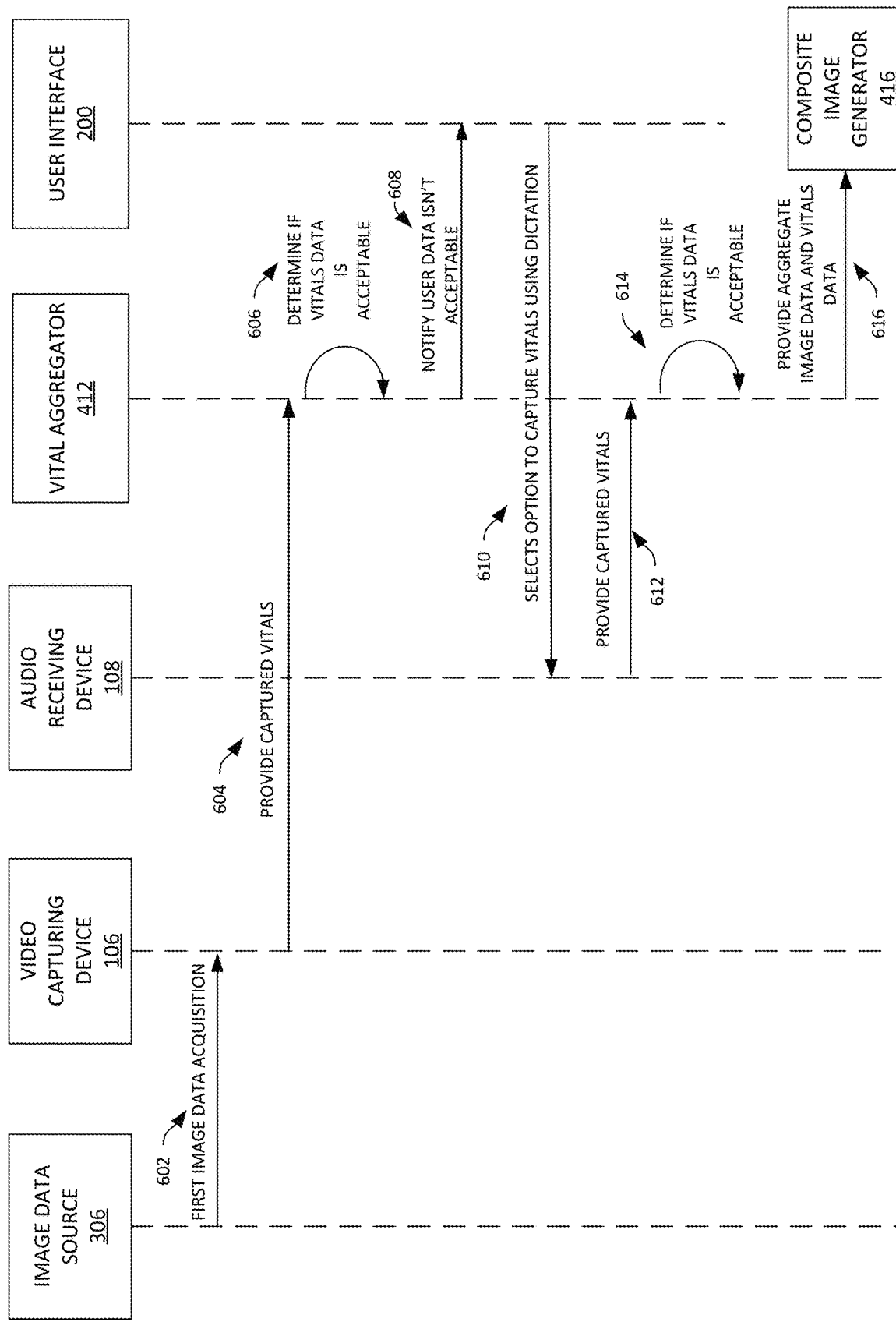

FIGS. 5 and 6 are example data flow diagrams showing an example exchange of information, instructions, and/or other messages between the example image data source 306, the example vitals capturing devices 106 and 108, the example vital aggregator 412, the example composite image generator 416, the example image archive 310, and the example user interface 200. The For example, the flow of data is represented by one arrow beginning at a first block and ending at a second block. The data flow is described in the examples below.

The data flow of FIG. 5 begins when the example image data source 306 is capturing an x-ray image. FIG. 5 is provided with example patients P1, P2, P3, and P4 at the example image data source 306 wherein each patient has a corresponding x-ray image in the image data source 306 and corresponding vitals data. In the example data flow of FIG. 5, at 502, the image data source 306 provides an image data acquisition trigger to trigger the vitals capturing 302 to capture a patient's vitals. For example, when the image data source 306 begins the process of capturing an x-ray image, the image data source 306 may notify a user (e.g., specialist 102) at the user interface 200 the vitals capturer 302 is available to be utilized. At 504, the vitals capturer 302 activates one and/or both of the vitals capturing devices 106, 108. In some examples, one vitals capturing device may be activated and the other is not. At 506, the image data source 306 provides image data of patient P1 to the example vital aggregator 412. At 508, the example vitals capturer 302 provides vitals data of patient P1 to the vitals aggregator 412. At 510, the example vitals aggregator 412 aggregates patient P1 vitals with the image data of P1. For example, the vital aggregator 412 may augment the vitals data into the DICOM header of the x-ray image, into the footer or the x-ray image, as a separate image attached to the x-ray image, etc. At 512, after the vital aggregator 412 aggregates patient P1 vitals with the image data, the example vitals aggregator 412 provides the patient P1 aggregate vitals and image data to the example composite image generator 416. At 514, the composite image generator 416 outputs the composite image to the image archive 310 and/or otherwise outputs the composite image for display, further processing, other storage/transmission, etc. For example, the composite image generator 416 may generate a readable image containing the patient P1's internal structures and vital data and send it via a network to the image archive 310. At 516, the example image archive 310 provides the composite image to a health care specialist to assess and diagnose the patient P1.

The data flow of FIG. 6 illustrates an example of the vitals aggregator 412 in communication with the example user interface 200 to provide acceptable data to the composite image generator 416. The data flow of FIG. 6, at 602, begins when the image data source 306 provides a first image data acquisition trigger to the video capturing device 106. In some examples, the image data source 306 can provide an image data acquisition trigger to the audio receiving device 108. For example, the user interface 200 can determine where the image data acquisition trigger is provided. At 604, the video capturing device 106 provides the captured vitals to the vitals aggregator 412. At 606, the vitals aggregator 412 determines if the vitals data is acceptable. For example, the vitals aggregator 412 can receive vitals data that was misconstrued by the example image processor 406 of FIG. 4 and detect the unacceptable data. The vitals aggregator 412 may utilize machine learning, a Bayesian network, a statistical model, etc. to detect the misconstrued data. At 608, the vitals aggregator 412 notifies the user interface 200 that the data was unacceptable. At 610, the user interface 200 prompts a user to select a method to capture patient vitals. For example, the user interface 200 may request that the user select the audio receiving device 108 because the video capturing device 106 was not processing data correctly, the lens was broken, etc. At 612, the audio receiving device provides the captured vitals to the vitals aggregator 412. At 614, the vitals aggregator 412 determines if the received vitals data is acceptable to aggregate with the image data. At 616, the vitals aggregator 412 provides the acceptable aggregate vitals data to the composite image generator 416.

A flowchart representative of example hardware logic, machine readable instructions, hardware implemented state machines, and/or any combination thereof for implementing the apparatus 300 of FIGS. 1-3B is shown in FIGS. 7, 8, 9, and 10. The machine readable instructions may be an executable program or portion of an executable program for execution by a computer processor such as the processor 1212 shown in the example processor platform 1200 discussed below in connection with FIG. 12. The program may be embodied in software stored on a non-transitory computer readable storage medium such as a CD-ROM, a floppy disk, a hard drive, a DVD, a Blu-ray disk, or a memory associated with the processor 1212, but the entire program and/or parts thereof could alternatively be executed by a device other than the processor 1212 and/or embodied in firmware or dedicated hardware. Further, although the example program is described with reference to the flowcharts illustrated in FIGS. 7, 8, 9, and 10 many other methods of implementing the example apparatus 300 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 7, 8, 9, and 10 may be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

FIGS. 7, 8, 9, and 10 are a flowcharts representative of example machine readable instructions which may be executed to implement the example aggregate apparatus 300 of FIGS. 1-3B to capture patient vitals during an x-ray procedure.

At block 702, the example aggregate system 300 loads a patient record. For example, the health care specialist may select the patient information box 204 on the patient selection display 202 by utilizing physical contact on a touch sensitive LCD display, a click of a mouse, etc. and the image data source 306 receives the patient selection.

In response to the loading a patient record, the example aggregate system 300 initiates an x-ray image capture at block 704. For example, the image data source 306 may need to load a patient record before the process of capturing an x-ray image begins, and initiating x-ray image capture initiates the process. At block 706, the image data source 306 triggers patient vitals capture. For example, capturing the vitals of a patient is pertinent when the patient is undergoing the process of x-ray capture, so when the x-ray image capture is initiated, the aggregate system 300 provides instructions to capture the patient vitals.

Figure 7:
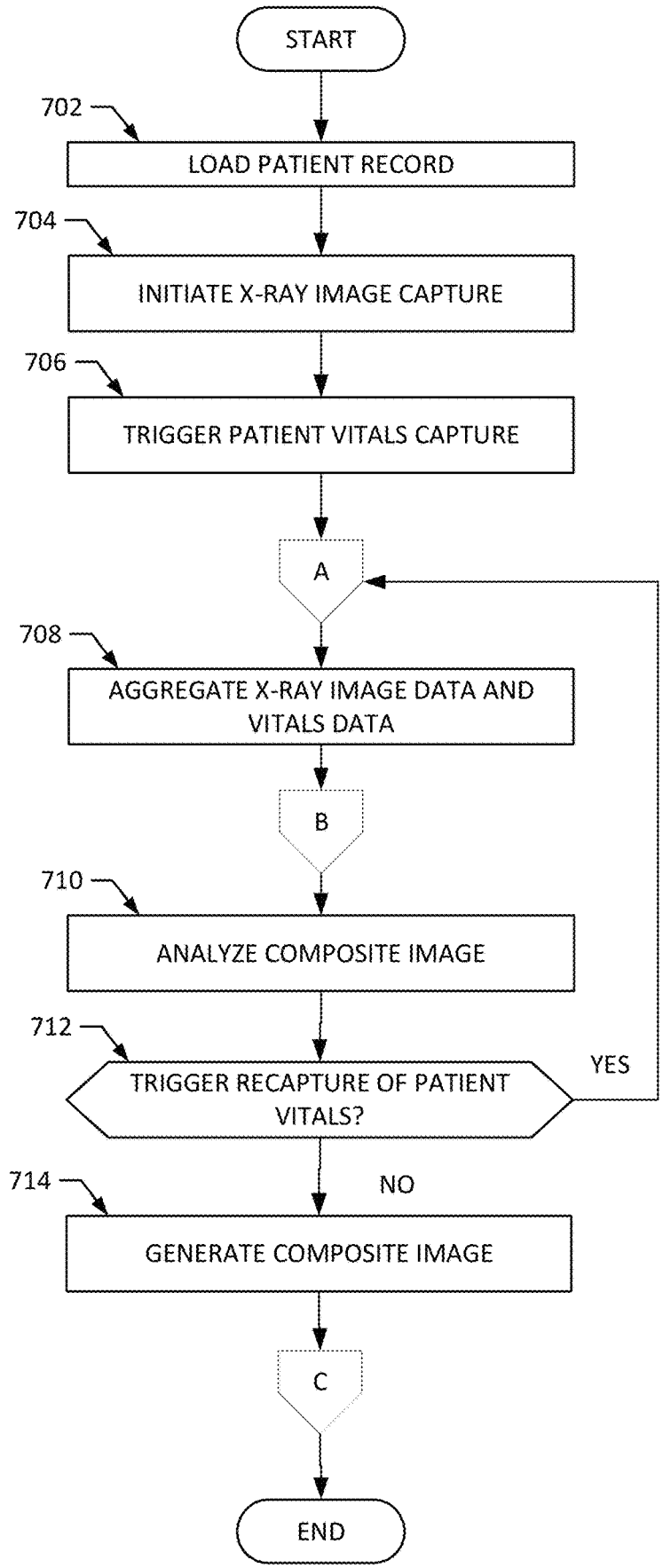
FIGS. 7, 8, 9, and 10 are flowcharts representative of machine readable instructions which may be executed to implement the aggregate system.
Figure 8:
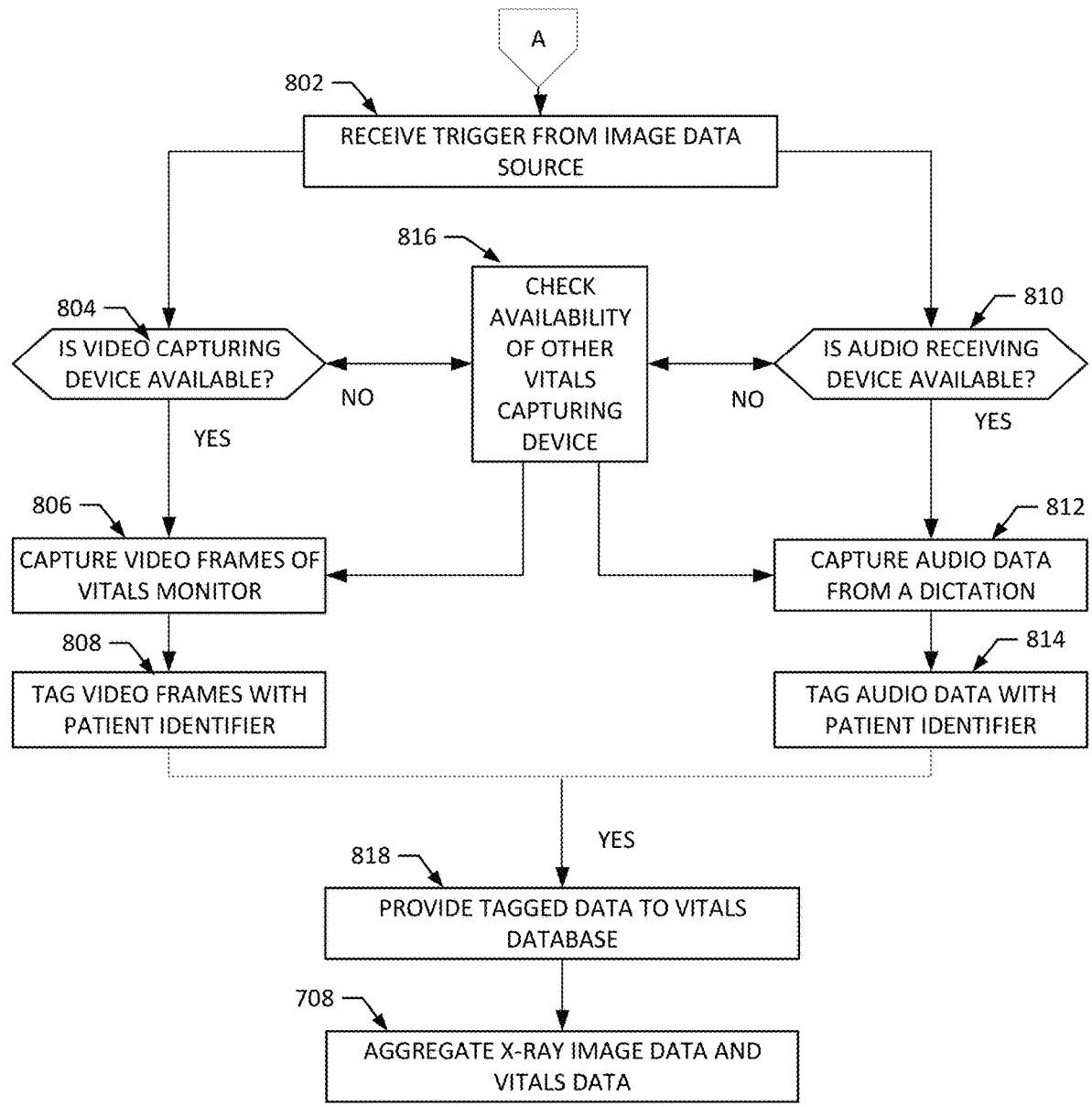

At block A, the process and instructions of FIG. 7 continue at block 802 of FIG. 1. The vitals capturer 302 receives the trigger from the image data source 306. For example, the trigger may be an instruction, a notification, etc. that provides power to the example vitals capturing devices 106, 108 of the vitals capturer 302. At block 804, the example vitals capturer 302 determines if the example video capturing device 106 is available. For example, the vitals capturer 302 may receive a request from a user interface to capture patient vitals utilizing the video capturing device 106. In this example, the vitals capturer 302 determines if the video capturing device 106 can be utilized. In some examples, the video capturing device 106 may be faulty with errors, not be connected to a power source, etc.

At block 806, the example vitals capturer 302 has determined the video capturing device 106 is available and the video capturing device 106 captures frames of the example vitals monitor 112 of FIG. 1. For example, the video capturing device 106 is previously positioned to focus on the vitals monitor 112. When the video capturing device 106 is activated, the device records the image in frames (e.g., number of images that are projected per second, per minute, etc.). At block 808, the vitals capturer 302 tags the video frames with a patient identifier. For example, the vitals capturer 302 augments or inserts metadata into the processed frame including a patient identifier that was provided by the image data source 306 after the patient was selected.

At block 818, the example vitals capturer 302 provides the tagged vitals data to the example vitals database 410 of FIG. 4. The tagged vitals data is stored in the example vitals database 410 in a manner in which the vitals data is always associated with the patient and easily accessible when the vitals of the patient are requested.

At block 810, the vitals capturer 302 determines if the example audio receiving device 108 is available. In some examples, the vitals capturer 302 may receive a request from a user interface 200 to capture patient vitals utilizing the audio receiving device 108. In this example, the vitals capturer 302 determines if the audio receiving device 108 can be utilized. In some examples, the audio receiving device 108 may be faulty with errors, not be connected to a power source, etc.

At block 812, the example vitals capturer 302 has determined the audio receiving device 108 is available and the audio receiving device 108 captures audio data from a dictation. For example, the specialist 102 begins to talk into the audio receiving device 108 and the speech processor records and transforms the sound waves 104 into audio signals that can be provided as useful information to a computer. At block 814, the example vitals capturer 302 tags the audio data with a patient identifier. For example, the vitals capturer 302 augments or inserts metadata into the processed audio data including a patient identifier that was provided by the image data source 306 after the patient was selected.

At block 818, the vitals capturer 302 provides with tagged vitals data to the example vitals database 410 of FIG. 4. The tagged vitals data is stored in the example vitals database 410 in a manner in which the vitals data is always associated with the patient and easily accessible when the vitals of the patient are requested.

At block 816, the example vitals capturer 302 determines the video capturing device 106 is not available and checks availability of the audio receiving device 108. In a different example, at block 816, the vitals capturer 302 has determined that the audio receiving device 108 is not available and checks availability of the video capturing device 106. This process can undergo a plurality of iterations until one of the vitals capturing devices is available to capture the patient's vitals. In some examples, if the vitals capture 302 has determined that a vital capturing device different than the one selected by the user is available, the example vitals capturer 302 notifies the user interface to provide a message to the user (e.g., specialist 102) that a different method of capturing patient vitals is to be utilized.

At block 708, the process returns to FIG. 7 and the vitals aggregator 412 aggregates the vitals data and the image data. For example, the vitals aggregator 412 may receive image data from the image data source 306 and process, tagged, and new vitals data from the vitals database 410.

Figure 9:
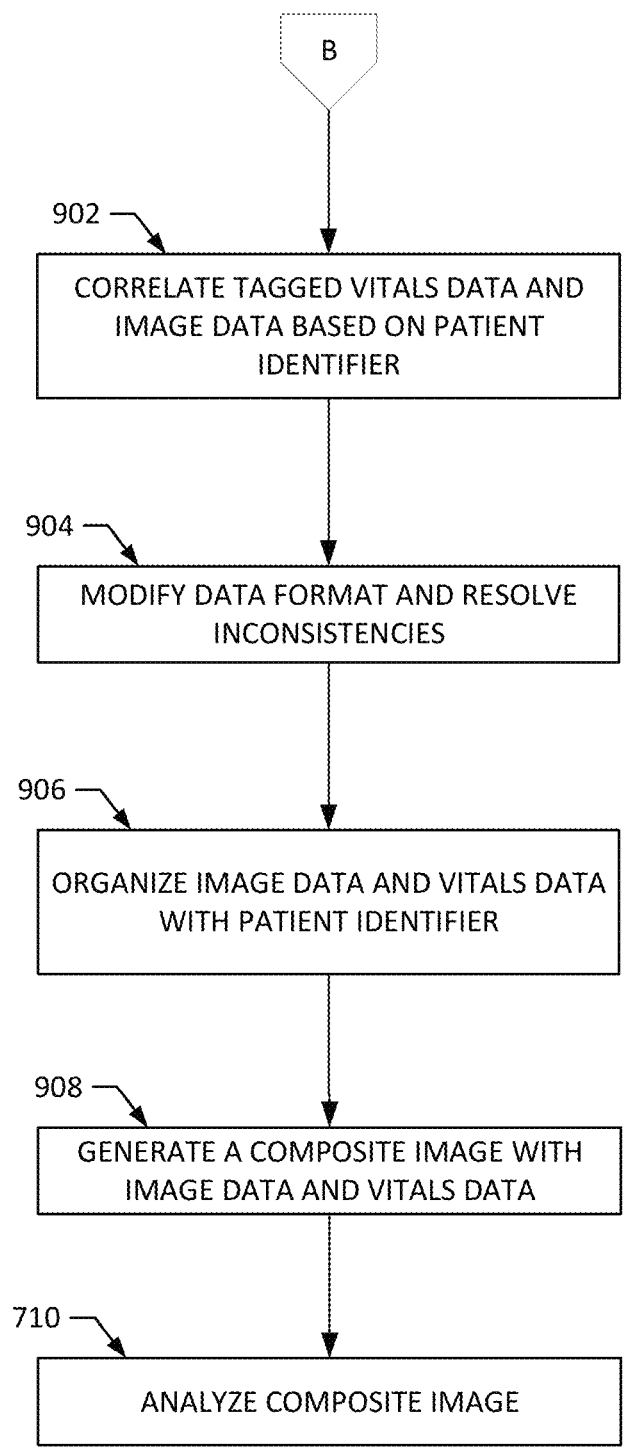
Figure 10:
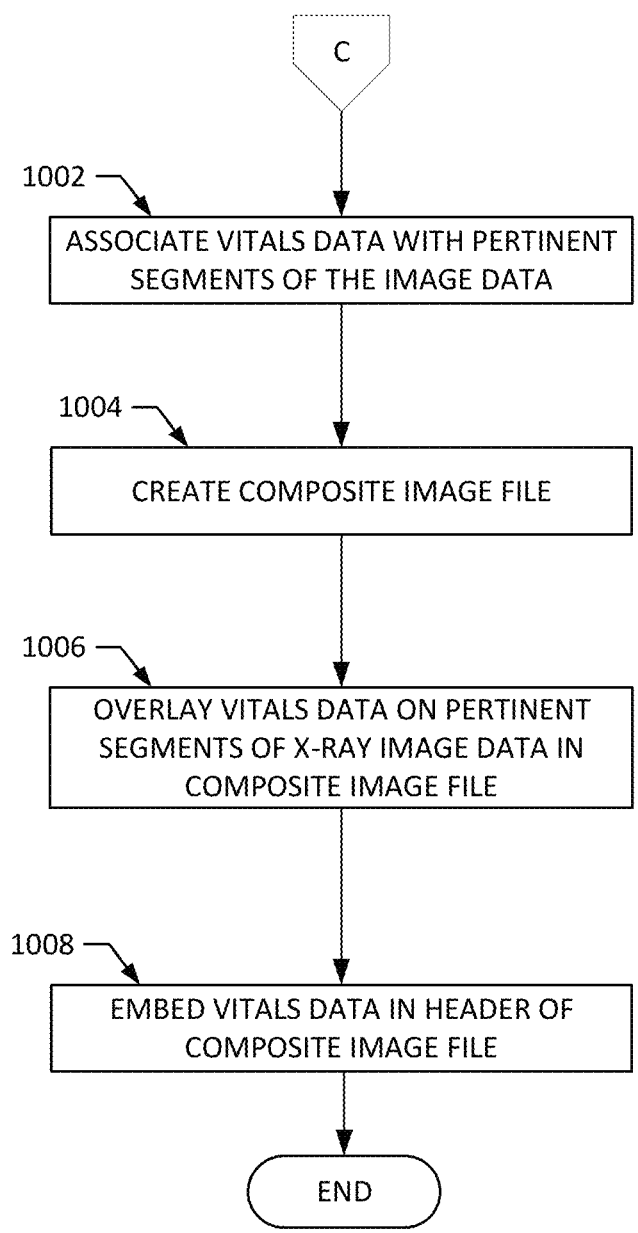

At block B, the process of aggregating the vitals data is described in FIG. 9 and begins at block 902. The example vitals aggregator 412 correlates the tagged vitals data and image data based on the patient identifier. For example, the vitals data is connected to the image data in which both the vitals data and the image data include the same patient identifier.

At block 904, the example vitals aggregator 412 modifies the vitals data format and resolves the inconsistencies. For example, the vitals data and image data can be difficult to read or misinterpreted by a receiving user if the data includes different numeric values of the same vital type (e.g., beats per minute, millimeters of mercury, etc.).

At block 906, the vitals aggregator 412 organizes the image data and vitals data with the patient identifier. For example, the vitals aggregator 412 provides the vitals data and image data with a new patient identifier type to augment the two data types. At block 908, the vitals aggregator 412 provides the aggregate vitals to the composite image generator 416 and the composite image generator 416 generates a composite image with the image data and vitals data. For example, the composite image generator 416 embeds the vitals data into the header of the image data to generate a composite image.

After the composite image is generated, the process returns to FIG. 7 at block 710, wherein the vitals aggregator 412 analyzes the composite image. For example, the vitals aggregator 412 analyzes the vitals data in the composite image to detect an anomaly by utilizing machine learning, a statistics model, previous historic data, etc. At block 712, the vitals aggregator 412 determines if the vitals capturer 302 needs to trigger a recapture of the patient vitals. For example, the vitals aggregator 412 determines if the vitals data in the composite image is anomalous based on the previous block 710. If the vitals aggregator 412 has determined there needs to be a recapture of patient vitals, the vitals aggregator triggers the vitals capturer 302 to activate one of the vitals capturing devices 106, 108 at block 706.

At block 714, if the example vitals aggregator 412 determines the data is not anomalous and a recapture does not need to occur, the composite image generator 416 generates the composite image. The example generating of the composite image is provided in the process of FIG. 10 and begins at block 1002.

At block 1002, the composite image generator 416 associated vitals data with pertinent segments of the image data. For example, the vitals data can be associated with the image data that includes the location of pixels, such as the pixels that will be positioned at the top of the image (e.g., the header). At block 1004, the composite image generator 416 creates and composite image file to store the associated vitals data with the image data as one. For example, by creating a composite image file, the composite image can be provided to any location or digital source.

At block 1006, the composite image generator 416 overlays the vitals data on the pertinent segments of the image data in the composite image file. As block 1008, composite image generator 416 embeds vitals data in the header of the composite image file. The composite image file is complete at the new x-ray image with corresponding patient vitals is provided to the image archive 306 for a receiving user to diagnose the patient associated with the image.

Figure 11:
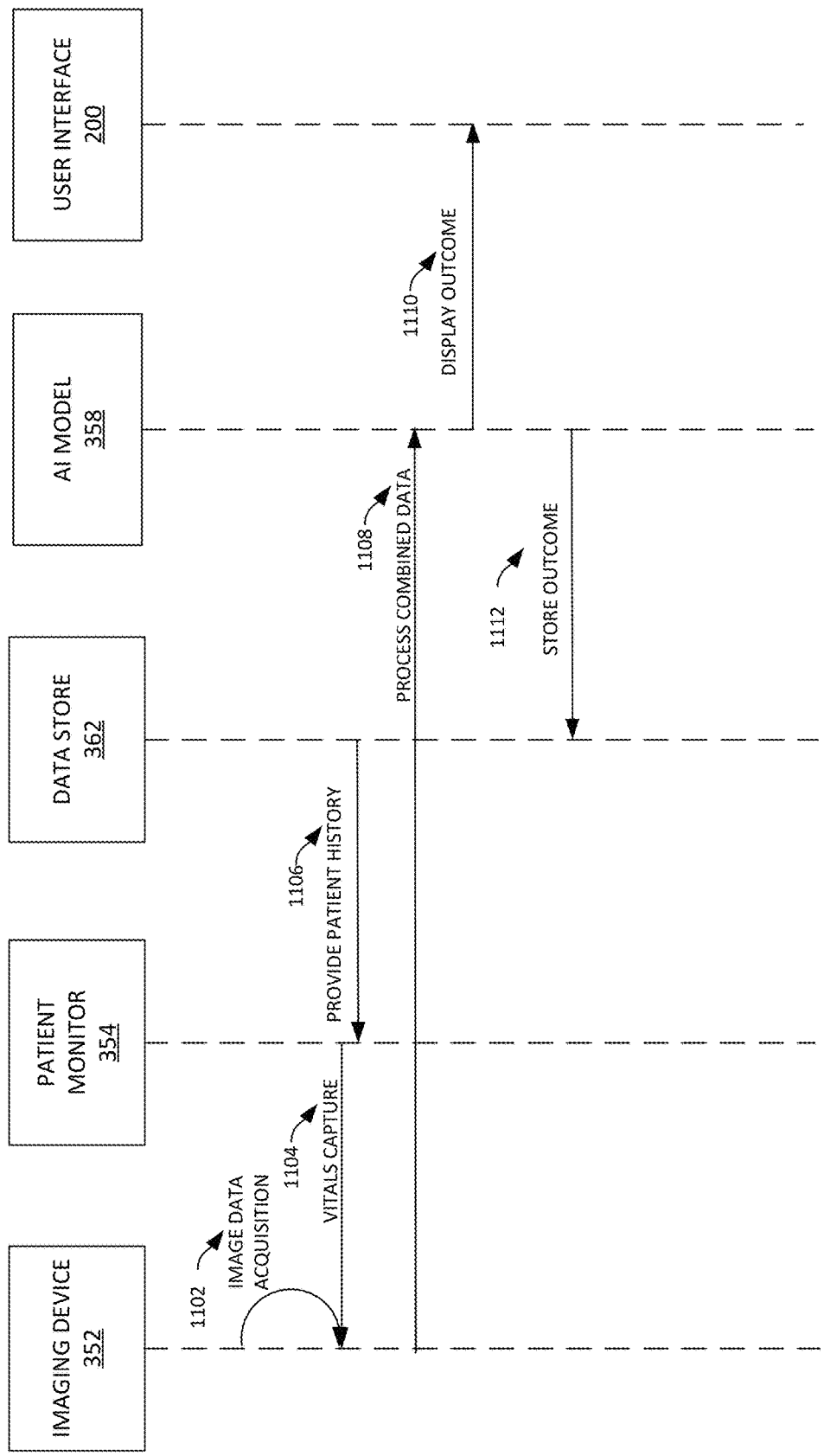
FIG. 11 is an example data flow diagram illustrating timing and flow of data and operations between the elements of the example of FIG. 3B.

As described above, the imaging device 352 can capture imaging and non-imaging data and process the combined set of data to drive a result. FIG. 11 illustrates an example data and timing flow 1100 of data gathering and processing using the example system 350. As shown in the example of FIG. 11, at 1102, at time T0, the imaging device 352 acquires imaging data. At 1104, at time T0, the imaging device 352 also captures patient vitals data from the patient monitor 354. At 1106, at time T1, the imaging device 352 retrieves patient history information from the data store 362. The retrieval can be based on patient identification, exam type, indicator from captured image and/or non-image data, etc. At 1108, at time T2, the AI model 358 processes the composite data set formed of image data, non-image data, and historical data. At 1110, an outcome or output can be displayed (e.g., on the example user interface 200, sent to another system to trigger a follow-up action such as an additional image capture, testing (e.g., blood work, blood pressure, other labs or physical testing, etc.), examination, etc. At 1112, the outcome/output is stored in the data store 362 (e.g., for retrieval, routing, processing, etc.).

As such, the imaging device 352, patient monitor 354, other sensor, etc., can publish acquired patient data (e.g., anonymized for population health gathering, identified for patient diagnosis/treatment, etc.) via the communication interface 354 to be used in combination for processing (e.g., AI model processing, etc.) to determine a diagnosis, treatment, trend (e.g., worsen/improve, worsen/improve by a certain degree or threshold, etc.), etc. The imaging device 352 and/or other device can serve as an information gathering hub in such an environment to gather data, process the data, trigger an alert, generate a composite image with embedded, tagged, and/or other formatted/processed information providing an actionable, data-rich image for AI network model processing (e.g., via CNN, RNN, other machine/deep learning network model, etc.). By gathering and combining the information, a single AI model can be used to evaluate an image and its embedded data, and/or multiple AI models can process the single composite image for multiple purposes, for example.

Figure 12:
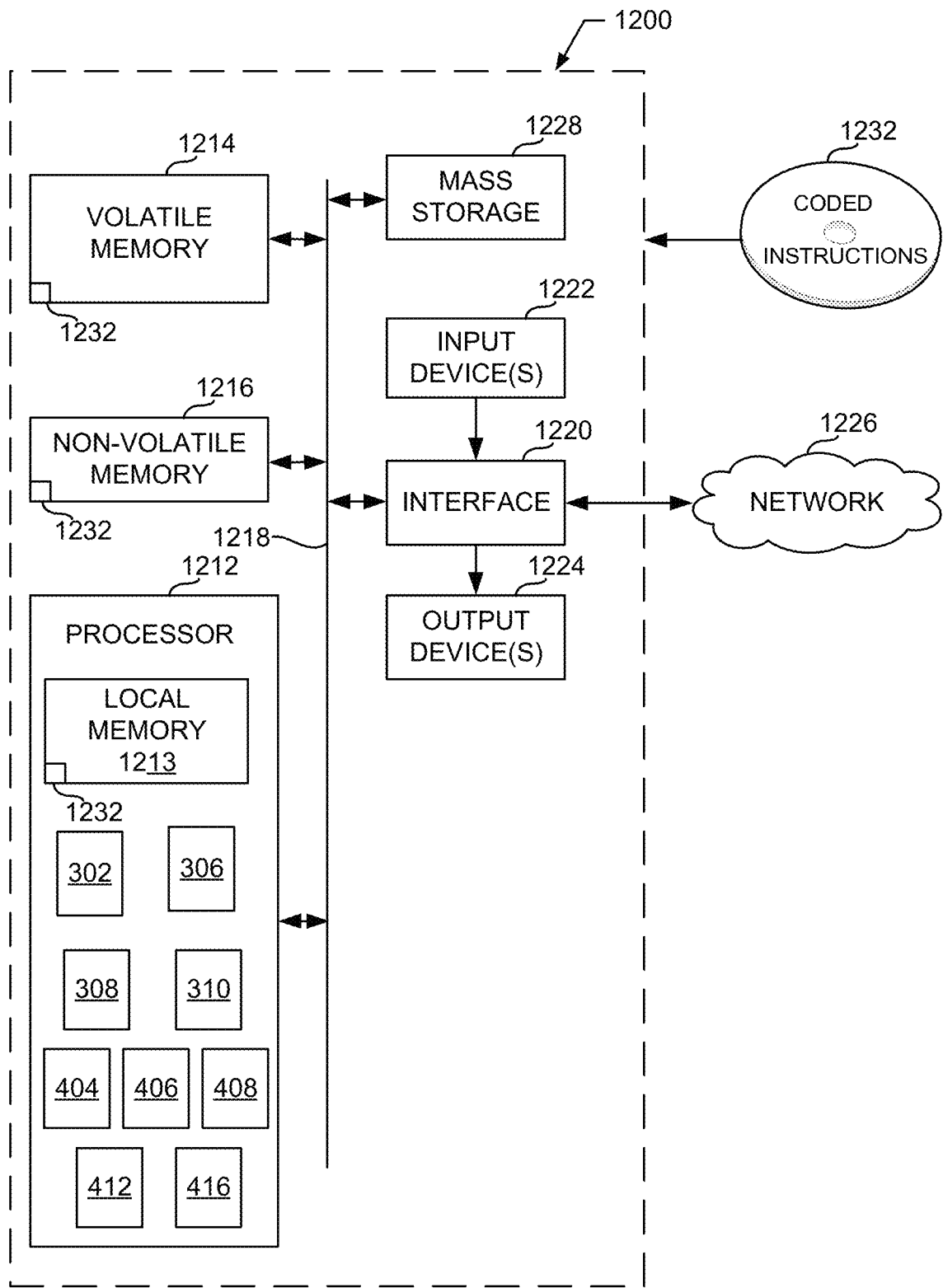
FIG. 12 is a block diagram of an example processing platform structured to execute the instructions of FIGS. 7, 8, 9, and 10 to implement the aggregate system.

FIG. 12 is a block diagram of an example processor platform 800 structured to execute the instructions of FIGS. 7, 8, 9, and 10 to implement the aggregate system 300 of FIGS. 1-3B. The processor platform 1200 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset or other wearable device, or any other type of computing device.

The processor platform 1200 of the illustrated example includes a processor 1212. The processor 1212 of the illustrated example is hardware. For example, the processor 1212 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1212 implements the example vitals capturer 302, the example image data source 306, the example vitals analyzer 308, the example image archive 310, the example speech processor 404, the example image processor 406, the example vitals data manager 408, the example vitals aggregator 412, and the example composite image generator 416. The example processor 1212 can similarly be used to implement the example imaging device 352, patient monitor 354, and/or data store 362 of the example of FIG. 3B.

The processor 1212 of the illustrated example includes a local memory 1213 (e.g., a cache). The processor 1212 of the illustrated example is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1216 may be implemented by flash memory and/or any other desired type of memory device. Access to the main memory 1214, 1216 is controlled by a memory controller.

The processor platform 1200 of the illustrated example also includes an interface circuit 1220. The interface circuit 1220 may be implemented by any type of interface standard, such as an Ethernet interface, a universal serial bus (USB), a Bluetooth® interface, a near field communication (NFC) interface, and/or a PCI express interface. The interface circuit 1220 may be used to implement the example communication interface 356 of the example of FIG. 3B.

In the illustrated example, one or more input devices 1222 are connected to the interface circuit 1220. The input device(s) 1222 permit(s) a user to enter data and/or commands into the processor 1212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to the interface circuit 1220 of the illustrated example. The output devices 1224 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1220 of the illustrated example, thus, typically includes a graphics driver card, a graphics driver chip and/or a graphics driver processor.

The interface circuit 1220 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1226. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, redundant array of independent disks (RAID) systems, and digital versatile disk (DVD) drives.

The machine executable instructions 1232 of FIGS. 7, 8, 9, and 10 may be stored in the mass storage device 1228, in the volatile memory 1214, in the non-volatile memory 1216, and/or on a removable non-transitory computer readable storage medium such as a CD or DVD.

From the foregoing, it will be appreciated that example methods, apparatus and articles of manufacture have been disclosed that improve a patient imaging and examination process by incorporating patient vitals information into an x-ray image to form a composite image such by capturing the vitals information in real-time during the x-ray imaging procedure. The disclosed methods, apparatus and articles of manufacture improve the efficiency of using a computing device by enabling real-time capture analysis of vitals information during an imaging procedure to reduce the time and increase the accuracy of reading an x-ray image. Certain examples improve an imaging device, such as a mobile imaging device, and its associated/included computing device/processor through the ability to acquire patient vitals information concurrently with patient image data and to combine the vitals information and image data to form a composite image for the patient. Certain examples alter the operation of an imaging device and associated processor to capture image data and vitals information, correlate the image data and vitals information, and generate a composite image. The disclosed methods, apparatus and articles of manufacture are accordingly directed to one or more improvement(s) in the functioning of a computer.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
an imaging device, triggered based on a patient record, to capture imaging data of a patient, the imaging device including at least one of an X-ray imaging device, an ultrasound imaging device, or a magnetic resonance imaging device;
a patient monitor to capture non-imaging data of the patient; and
a communication interface between the imaging device and the patient monitor to route the non-imaging data to the imaging device,
wherein the imaging device is to combine the non-imaging data with the imaging data to form a combined data set to be processed in a context formed from patient history of the patient record to determine a clinical outcome.

2. The apparatus of claim 1, wherein the imaging data and the non-imaging data are captured at a same time.

3. The apparatus of claim 1, wherein the communication interface between the imaging device and the patient monitor is bi-directional.

4. The apparatus of claim 1, wherein the communication interface is a wireless communication interface between an imaging device receiver and a patient monitor transmitter.

5. The apparatus of claim 1, wherein the imaging device includes an artificial intelligence model to process the combined data set to determine the clinical outcome.

6. The apparatus of claim 5, wherein the artificial intelligence model is a first artificial intelligence model, and wherein the imaging device includes a second artificial intelligence model to process the captured non-imaging data for combination with the imaging data.

7. The apparatus of claim 1, wherein the combined data set is formed as a composite image with the non-imaging data embedded in an image formed from the imaging data.

8. The apparatus of claim 1, wherein the imaging device includes at least one of a camera or a microphone, and wherein the non-imaging data is captured by the imaging device using at least one of the camera or the microphone.

9. The apparatus of claim 1, wherein the imaging data includes x-ray imaging data and the non-imaging data includes patient oxygen saturation information.

10. The apparatus of claim 1, wherein the clinical outcome includes a trend in at least one of a condition or a disease.

11. The apparatus of claim 10, wherein the trend is displayed in conjunction with an image formed from the imaging data.

12. A non-transitory computer readable storage medium comprising instructions that, when executed, cause at least one imaging device processor to at least:
capture, triggered based on a patient record, imaging data of a patient;
capture non-imaging data of the patient via a communication interface between the at least one imaging device processor and a patient monitor;
combine the non-imaging data with the imaging data to form a combined data set; and
facilitate processing of the combined data set in a context formed from patient history of the patient record to determine a clinical outcome,
wherein the imaging device processor is incorporated into at least one of an X-ray imaging device, an ultrasound imaging device, or a magnetic resonance imaging device.

13. The computer readable storage medium of claim 12, wherein the imaging data and the non-imaging data are captured at a same time.

14. The computer readable storage medium of claim 12, wherein the communication interface is a wireless communication interface between an imaging device receiver and a patient monitor transmitter.

15. The computer readable storage medium of claim 12, wherein the at least one processor interacts with an artificial intelligence model to process the combined data set to determine the clinical outcome.

16. The computer readable storage medium of claim 15, wherein the artificial intelligence model is a first artificial intelligence model, and wherein the at least one processor interacts with a second artificial intelligence model to process the captured non-imaging data for combination with the imaging data.

17. The computer readable storage medium of claim 12, wherein the combined data set is formed as a composite image with the non-imaging data embedded in an image formed from the imaging data.

18. The computer readable storage medium of claim 12, wherein the non-imaging data is captured using at least one of a camera or a microphone.

19. A method comprising:
   capturing, using an imaging device and triggered based on a patient record, imaging data of a patient;
   capturing, using the imaging device, non-imaging data of the patient via a communication interface between the imaging device and a patient monitor;
   combining, using the imaging device, the non-imaging data with the imaging data to form a combined data set; and
   facilitating processing of the combined data set in a context formed from patient history of the patient record to determine a clinical outcome,
   wherein the imaging device includes at least one of an X-ray imaging device, an ultrasound imaging device, or a magnetic resonance imaging device.

20. The method of claim 19, wherein the processing includes using at least one artificial intelligence model to determine the clinical outcome from the combined data set.

* * * * *